(12) United States Patent
Ottosen et al.

(10) Patent No.: US 6,313,174 B1
(45) Date of Patent: Nov. 6, 2001

(54) AMINOBENZOPHENONES AS INHIBITORS OF INTERLEUKIN AND TNF

(75) Inventors: Erik Rytter Ottosen, Ølstykke; Schneur Rachlin, Melby, both of (DK)

(73) Assignee: Leo Pharmaceutical Products Ltd.A/S/ (Løvens kemiske Fabrik Produktionsaktieselskab), Ballerup (DK)

( * ) Notice: Subject to any disclaimer, the term of this patent is extended or adjusted under 35 U.S.C. 154(b) by 0 days.

(21) Appl. No.: 09/341,923
(22) PCT Filed: Jan. 8, 1998
(86) PCT No.: PCT/DK98/00008
§ 371 Date: Jul. 21, 1999
§ 102(e) Date: Jul. 21, 1999
(87) PCT Pub. No.: WO98/32730
PCT Pub. Date: Jul. 30, 1998

(30) Foreign Application Priority Data

Jan. 24, 1997 (GB) .................................... 9701453

(51) Int. Cl.[7] ........................ C07C 225/22; A61K 31/135
(52) U.S. Cl. .......................................... 514/646; 564/319
(58) Field of Search .............................. 564/319; 514/646

(56) References Cited

FOREIGN PATENT DOCUMENTS 37 39 402   6/1988  (DE) .
1 535 401   12/1978 (GB) .

Primary Examiner—Paul J. Killos

(74) Attorney, Agent, or Firm—Pillsbury Winthrop LLP

(57) ABSTRACT

The compounds of the present invention are represented by general formula (I) in which formula $R_1$ and $R_2$ stand independently for one or more, similar or different substituents selected from the group consisting of hydrogen, halogen, hydroxy, mercapto, trifluoromethyl, amino, alkyl, alkoxy, alkylthio, alkylamino, or alkoxycarbonyl, the C-content of which can be from 1 to 5, cyano, carboxy, carbamoyl, phenyl, or nitro; $R_3$ stands for hydrogen, halogen, hydroxy, mercapto, trifluoromethyl, amino, alkyl, alkoxy, alkylthio, alkylamino, or alkoxycarbonyl, the C-content of which can be from 1 to 5, phenyl, cyano, carboxy, or carbamoyl; $R_4$, $R_5$ and $R_6$ stand independently for hydrogen, trifluoromethyl, alkyl, carbamoyl, alkoxycarbonyl, or alkyloxo, the C-content of which can be from 1 to 5; X stands for oxygen, N—OH, N—O-alkyl, dialkoxy, cyclic dialkoxy, dialkylthio, or cyclic dialkylthio, the C-content of which can be from 1 to 5. The present compounds are of value in the human and veterinary practice as systemic and topical therapeutic agents for the treatment and prophylaxis of asthma, allergy, rheumatoid arthritis, spondyloarthritis, gout, atherosclerosis, chronic inflammatory bowel disease, proliferative and inflammatory skin disorders, such as psoriasis, and atopic dermatitis.

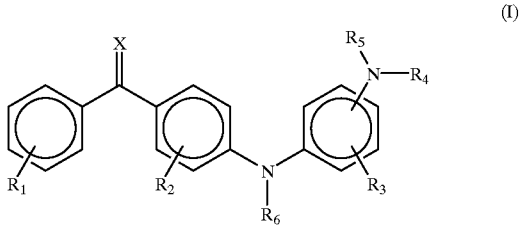

(I)

7 Claims, No Drawings

AMINOBENZOPHENONES AS INHIBITORS OF INTERLEUKIN AND TNF

This application is the national phase of international application PCT/DK98/00008 filed Jan. 8, 1998 which designated the U.S.

This invention relates to a hitherto unknown class of compounds which shows anti-inflammatory effects, to pharmaceutical preparations containing these compounds, to dosage units of such preparations, and to their use in the treatment and prophylaxis of asthma, allergy, rheumatoid arthritis, spondyloarthritis, gout, atherosclerosis, chronic inflammatory bowel disease, proliferative and inflammatory skin disorders, such as psoriasis, and atopic dermatitis.

The compounds of the present invention are represented by the general formula I

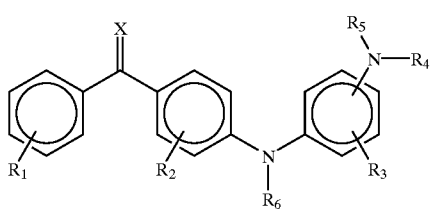

in which formula $R_1$ and $R_2$ stands independently for one or more, similar or different substituents selected from the group consisting of hydrogen, halogen, hydroxy, mercapto, trifluoromethyl, amino, alkyl, alkoxy, alkylthio, alkylamino, and alkoxycarbonyl, the C-content of which can be from 1 to 5, cyano, carboxy, carbamoyl, phenyl, or nitro; $R_3$ stand for hydrogen, halogen, hydroxy, mercapto, trifluoromethyl, amino, alkyl, alkoxy, alkylthio, alkylamino, or alkoxycarbonyl, the C-content of which can be from 1 to 5, phenyl, cyano, carboxy, or carbamoyl; $R_4$, $R_5$ and $R_6$ stands independently for hydrogen, trifluoromethyl, alkyl, carbamoyl, alkoxycarbonyl, or alkyloxo, the C-content of which can be from 1 to 5; X stands for oxygen, N—OH, N—O—alkyl, dialkoxy, cyclic dialkoxy, dialkylthio, or cyclic dialkylthio, the C-content of which can be from 1 to 5.

The compounds can be used in the form of their salts which are formed with pharmaceutically acceptable inorganic or organic acids, such as hydrochloric, hydrobromic and hydroiodic acid, phosphoric acid, sulphuric acid, nitric acid, p-toluenesulphonic acid, methanesulphonic acid, formic acid, acetic acid propionic acid, citric acid, tartaric acid, succinic acid, benzoic acid, maleic acid, these examples being considered as non-limiting for the invention.

Previously, a series of closely related aminobenzophenones (e.g. 4-(2-amnino4-nitrophenylamino)benzophenone) have been described (Hussein, F. A. et al, Iraqi J. Sci., 22, 54–66 (1981)). However, there is no description of their uses.

Now we have surprisingly found that novel aminobenzophenones according to general formula I are potent inhibitors of interleukin 1β (IL-1β) and tumour necrosis factor α (TNF-α) secretion in vitro, making them potentially useful for treatment of inflammatory diseases, in which the production of cytokines is involved in the pathogenesis, e.g. asthma, rheumatoid arthritis, psoriasis, contact dermatitis, and atopic dermatitis.

To study the effect of the compound of the present invention, in vitro, the inhibition of the IL-1β and TNF-α secretion was measured using the following procedure:

Cytokine production was measured in the media from lipopolysaccharide (LPS) stimulated peripheral blood mononuclear cells. The mononuclear cells were isolated from human peripheral blood by Lymphoprep® (Nycomed, Norway) fractionation and suspended in RPMI 1640 (growth medium) with foetal calv serum (FCS, 2%), at a concentration of 5×10⁵ cells/ml. The cells were incubated in 24-well tissue culture plates in 1 ml aliquots. Test compounds were dissolved in dimethylsulfoxide (DMSO, 10 mM) and were diluted with the medium. Compounds were added to the cells for 30 minutes, then LPS (1 μg/ml final concentration) was added. The plates were incubated for 18 hours, and the concentration of IL-1β and TNF-α in the medium was determined by enzyme-linked immunosorbent assays. The median inhibitory concentrations ($IC_{50}$) of the compounds were calculated. The results are shown in table 1.

The compounds of the present invention also show similar activities in the ability to inhibit PMN (polymorphonuclear) superoxide secretion which is also indicative of potentially useful anti-inflammatory drugs. The compounds were tested using the following procedure:

Human polymorphonuclear (PMN) granulocytes were isolated from human blood by dextran sedimentation, Lymphoprep® fractionation and hypotonic lysis of contaminating erythrocytes.

Superoxide anion generation was measured as the superoxide dismutase inhibitable reduction of ferricytochrome C (Madhu, S. B. et al, Inflammation, 16, 241, (1992)).

The cells were suspended in Hanks' balanced salt solution, and incubated for 10 minutes at 37° C. with test compounds. The cells were primed by the addition of TNF-α (3 ng/ml final concentration) for 10 minutes, and then ferricytochrome C, (final concentration 750 μg/ml), bovine serum albumin (BSA, final concentration 1 mg/ml) and formyl-methionyl-leucyl-phenylalanine (fMLP, final concentration $10^{-7}$ M) were added for 3 minutes.

The cells were chilled on ice, and were spun down. The optical densities in the cell-free supernatant was measured in a spectrophotometer.

The median inhibitory concentration ($IC_{50}$) of the compounds was calculated. The results are shown in Table 1.

TABLE 1

Inhibition of cytokines and PMN-superoxide production in vitro by compounds of the following examples of the present invention.

| | The median inhibition concentration ($IC_{50}$, nM) of | | |
|---|---|---|---|
| Compound from | IL-1β | TNF-α | PMN-superoxide |
| Example no. 1 | 250 | 790 | 160 |
| Example no. 13 | 160 | 200 | 40 |
| Example no. 32 | 100 | 130 | >10000 |
| Example no. 56 | 13 | 7.1 | 5.0 |
| Example no. 73 | 32 | 5.0 | 5.0 |

These results show that the compounds of the present invention are able to inhibit the production of IL-1, TNF-α and PMN-superoxide, thus making them potentially useful in the treatment of inflammatory diseases.

To study the compounds of the present invention in vivo the 12—O—tetradecanoylphorbol-13-acetate (TPA) induced murine chronic skin inflammation model were used (De Young, L. M. et al, Agents Actions, 26, 335–341 (1989); Carlson, R. P. et al, Agents Actions, 17, 197–204 (1985); Alford, J. G. et al, Agents Action, 37, (1992); Stanley, P. L. et al, Skin Pharmacol, 4, 262–271 (1991)). The compounds were tested using the following procedure:

In groups of 6 female mice weighing 18–25 grams, ear skin inflammation was induced by multiple topical applications of TPA on alternate days during a 10 day period. The resulting inflammation was treated topically with compounds in acetone (20 μl/ear) twice daily on day 8, 9 and 10 and once on day 11. The increased ear thickness (ET, right ear thickness minus left ear thickness) was determined approximately 6 hours after the treatment, the mice were sacrificed and the myeloperoxidase (MPO)-activity was determined in ear biopsies. The results are shown in Table 2.

TABLE 2

Effect in the TPA induced murine skin inflammation model by compounds of the following examples of the present invention.

| Compound from | Dose (mg/ear) | % inhibition of ET | % inhibition of MPO |
|---|---|---|---|
| Example no. 1 | 0.1 | 50 | 65 |
| Example no. 2 | 0.1 | 40. | 76 |
| Example no. 27 | 0.1 | 44 | 48 |
| Hydrocortisone | 0.1[a] | 58 | 69 |
|  | 0.03 | 36 | 51 |

[a]Reduction of spleen and thymus weight.

These results shows that the compounds of the present invention are of the same potency compared to known reference compounds, e.g. hydrocortisone with its known side effects, whereas the compounds of the present invention are well tolerated and are non-toxic. Some members of the present class of compounds show a very low absorption, thus making them especially useful in the treatment of various dermatological diseases. In general, they may be administered by oral, intravenous, interperitoneal, intranasal, topically or transdermal routes.

The present invention also relates to methods for preparing the desired compounds of the general formula I. The compounds of the formula I may conveniently be prepared by standard procedures detailed in the art. The routes are outlined in the following reaction scheme.

Scheme 1: Synthesis of the compounds of the general formula I

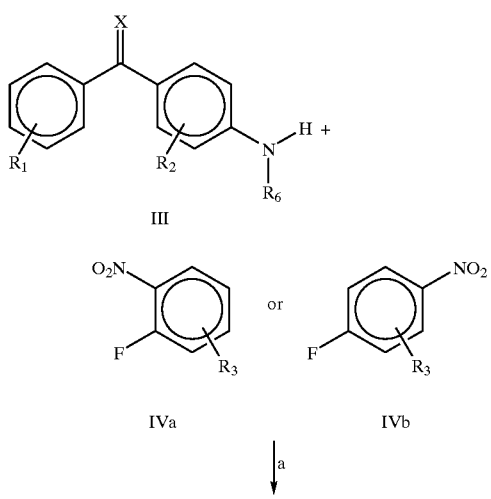

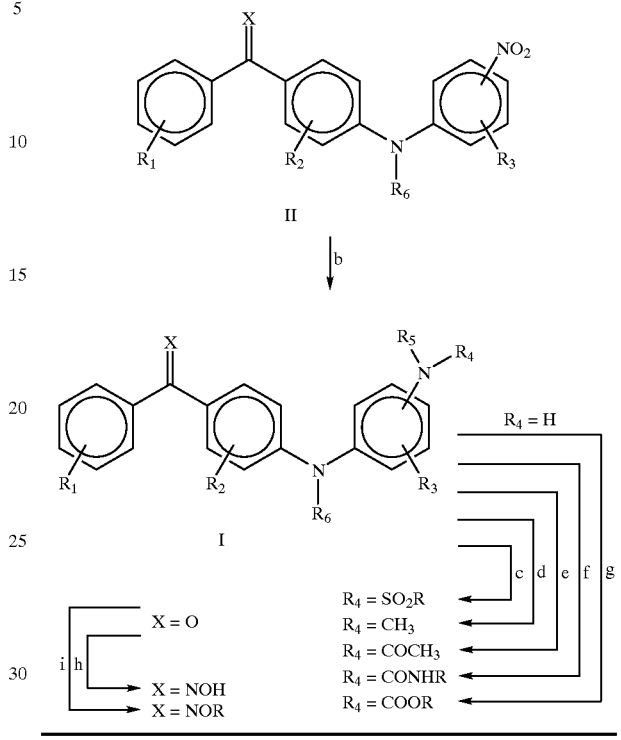

Notes to scheme 1
a Potassium tert-butoxide/dimethylsulfoxide/20° C./24–60 hours
b Hydrazine hydrate/10% Pd/C/ethanol/20° C./24 hours or Stannous chloride dihydrate/ethanol/70° C./1–4 hours
c Alkyl- or aryl-sulfonyl chloride/pyridine/20° C./60–120 min
d Alkyl halogenide/potassium carbonate/N,N-dimethylformamide/20° C./96 hours
e Acetic anhydride/20° C./3 hours
f Alkyl- or aryl-isocyanate/toluene/100° C./20 hours
g Alkyl- or aryl-chloroformate/potassium carbonate/N,N-dimethylformamide/20° C./96 hours
h Hydroxylamine hydrochloride/ethanol/sodium acetate/reflux/20° C./30 hours
i O-Methylhydroxylamine hydrochloride/ethanol/sodium aetate/reflux/20° C./25 hours The present compounds are intended for use in pharmaceutical compositions which are useful in the treatment of the above mentioned diseases.

The amount required of a compound of formula I (hereinafter referred to as the active ingredient) for therapeutic effect will, of course, vary both with the particular compound, the route of administration and the mammal under treatment. A suitable dose of a compound of formula I for systemic treatment is 0.1 to 200 mg/kg bodyweight, the most preferred dosage being 0.2 to 50 mg/kg of mammal bodyweight, administered one or more times daily.

While it is possible for an active ingredient to be administered alone as the raw chemical, it is preferable to present it as a pharmaceutical formulation. Conveniently, the active ingredient comprises from 0.1% to 100% by weight of the formulation. Conveniently, dosage units of a formulation contain between 0.07 mg and 1 g of the active ingredient. For topical administration, the active ingredient preferably comprises from 1% to 20% by weight of the formulation but the active ingredient may comprise as much as 50% w/w. Formulations suitable for nasal or buccal administration may comprise 0.1% to 20% w/w. for example about 2% w/w of active ingredient.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and human medical use, of the present invention comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include those in a form suitable for oral, ophthalmic, rectal, parenteral (including subcutaneous, intramuscular and intravenous), transdermal, intra-articular, topical, nasal, or buccal administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra articular and ophthalmic administration.

Formulations suitable for topical administration, including eye treatment, include liquid or semi-liquid preparations such as liniments, lotions, gels, applicants oil-in-water or water-in-oil emulsions such as creams, ointments or pastes; or solutions or suspensions such as drops.

Formulations suitable for administration to the nose or buccal cavity include powder, self-propelling and spray formulations, such as aerosols and atomizers.

In addition the aforementioned ingredients, the formulations of this invention may include one or more additional ingredients.

The compositions may further contain other therapeutically active compounds usually applied in the treatment of the above mentioned pathological conditions, for instance glucocorticoids, vitamin D's, anti-histamines, platelet activating factor (PAF) antagonists, anticolinergic agents, methyl xanthines, β-adrenergic agents, salicylates, indomethacin, flufenamate, naproxen, timegadine, gold salts, penicillamine, serum cholesterol-reducing agents, retinoids, zinc salts, and salicylazosulfapyridin (Salazopyrin).

The invention will now be further described in the following non-limiting general procedures, preparations and examples:

General procedures, preparations and examples

The exemplified compounds I are listed in table 3, whereas compounds of the general formula II are listed in table 4

All melting points are uncorrected. For $^1$H and $^{13}$C nuclear magnetic resonance (NMR) spectra (300 MHz) chemical shift values (δ) are quoted, unless otherwise specified, for deuteriochloroform and hexadeuterodimethylsulfoxide solutions relative to internal tetramethylsilane (δ0.00) or chloroform ($^1$H NMR δ7.25, $^{13}$C NMR δ76.81). The value for a multiplet (m), either defined (doublet (d), triplet (t), quartet (q)) or not at the approximate mid point is given unless a range is quoted (s singlet, b broad). Chromatography was performed on silica gel.

TABLE 3

| Comp. No. | Example No. | General formula | Position of $NR_4R_5$ | X | $R_1$ | $R_2$ | $R_3$ | $R_4$ | $R_5$ | $R_6$ |
|---|---|---|---|---|---|---|---|---|---|---|
| 101 | 1 | I | 2 | O | H | H | H | H | H | H |
| 102 | 2 | I | 4 | O | H | H | H | H | H | H |
| 103 | 3 | I | 2 | O | H | H | 4-Me | H | H | H |
| 104 | 4 | I | 2 | O | H | H | 4-$CF_3$ | H | H | H |
| 105 | 5 | I | 2 | O | H | H | 4-COOH | H | H | H |
| 106 | 6 | I | 4 | O | H | H | 2-CN | H | H | H |
| 107 | 7 | I | 4 | O | H | H | 2-COOH | H | H | H |
| 108 | 8 | I | 4 | O | H | H | 2-Me | H | H | H |
| 109 | 9 | I | 2 | O | 2-F | H | H | H | H | H |
| 110 | 10 | I | 2 | O | 4-F | H | H | H | H | H |
| 111 | 11 | I | 2 | O | 4-t-Bu | H | H | H | H | H |
| 112 | 12 | I | 2 | O | 3-F | H | H | H | H | H |
| 113 | 13 | I | 2 | O | 2-Cl | H | H | H | H | H |
| 114 | 14 | I | 2 | O | 3-Cl | H | H | H | H | H |
| 115 | 15 | I | 2 | O | 2-OMe | H | H | H | H | H |
| 116 | 16 | I | 2 | O | 3-N(Me)2 | H | H | H | H | H |
| 117 | 17 | I | 2 | O | 4-Cl | H | H | H | H | H |
| 118 | 18 | I | 2 | O | 3-Me | H | H | H | H | H |
| 119 | 19 | I | 4 | O | H | 3-$NH_2$ | H | H | H | H |

TABLE 3-continued

| Comp. No. | Example No. | General formula | Position of NR₄R₅ | X | R₁ | R₂ | R₃ | R₄ | R₅ | R₆ |
|---|---|---|---|---|---|---|---|---|---|---|
| 120 | 20 | I | 2 | O | 4-n-pentyl | H | H | H | H | H |
| 121 | 21 | I | 2 | O | 4-Cl; 2-SCH(Me)₂ | H | H | H | H | H |
| 122 | 22 | I | 2 | O | 4-CF₃ | H | H | H | H | H |
| 123 | 23 | I | 2 | O | H | H | H | SO₂Et | H | H |
| 124 | 24 | I | 2 | O | H | H | H | SO₂Ph | H | H |
| 125 | 25 | I | 4 | O | H | H | H | SO₂Me | H | H |
| 126 | 26 | I | 2 | O | H | H | H | SO₂Me | H | H |
| 127 | 27 | I | 2 | O | H | H | H | SO₂Ph-4-Me | H | H |
| 128 | 28 | I | 2 | O | H | H | H | CONHPh | H | H |
| 129 | 29 | I | 2 | O | H | H | H | Ac | H | H |
| 130 | 30 | I | 2 | N—OH | H | H | H | H | H | H |
| 131 | 31 | I | 2 | N—OMe | H | H | H | H | H | H |
| 132 | 32 | I | 2 | O | H | H | H | COOEt | H | H |
| 133 | 33 | I | 2 | O | H | H | H | CH₂COOEt | H | H |
| 134 | 34 | I | 2 | O | H | H | H | Me | H | H |
| 135 | 35 | I | 2 | O | H | H | H | Me | Me | H |
| 136 | 36 | I | 2 | O | 3,4,5-tri-OMe | H | H | H | H | H |
| 137 | 37 | I | 2 | O | H | H | H | H | H | Me |
| 138 | 38 | I | 2 | O | 2-Me | H | H | H | H | H |
| 139 | 39 | I | 2 | O | 3,4(OCH₂)₂ | H | H | H | H | H |
| 140 | 40 | I | 2 | O | 4-Cl | 2-Cl | H | H | H | H |
| 141 | 41 | I | 2 | O | 2,4-di-Cl | H | H | H | H | H |
| 142 | 42 | I | 2 | O | 4-(1-methylbutyloxy) | H | H | H | H | H |
| 143 | 43 | I | 2 | O | 3-CF₃ | H | H | H | H | H |
| 144 | 44 | I | 2 | O | 2,3-di-OMe | H | H | H | H | H |
| 145 | 45 | I | 2 | O | 3-n-BuO | H | H | H | H | H |
| 146 | 46 | I | 2 | O | 4-OEt | H | H | H | H | H |
| 147 | 47 | I | 2 | O | 3,5-di-Cl | H | H | H | H | H |
| 148 | 48 | I | 2 | O | 4-OCH₂Ph | H | H | H | H | H |
| 149 | 49 | I | 2 | O | 3-OMe, 4-Me | H | H | H | H | H |
| 150 | 50 | I | 4 | O | H | H | 2-Cl | H | H | H |
| 151 | 51 | I | 2 | O | 4-OMe | H | H | H | H | H |
| 152 | 52 | I | 2 | O | H | 2-Cl | H | H | H | H |
| 153 | 53 | I | 2 | O | H | 3-Me | H | H | H | H |
| 154 | 54 | I | 2 | O | 3-Ph | H | H | H | H | H |
| 155 | 55 | I | 2 | O | 2-Ph | H | H | H | H | H |
| 156 | 56 | I | 2 | O | 2-Me | 2-Cl | H | H | H | H |
| 157 | 57 | I | 2 | O | 4-Ph | H | H | H | H | H |
| 158 | 58 | I | 2 | O | H | H | 5-OH | H | H | H |
| 159 | 59 | I | 2 | O | 2-OH | H | H | H | H | H |
| 160 | 60 | I | 4 | O | 2-Me | H | H | H | H | H |
| 161 | 61 | I | 2 | O | 3-CN | H | H | H | H | H |
| 162 | 62 | I | 2 | O | 2-CH₂OPh | H | H | H | H | H |
| 163 | 63 | I | 2 | O | 2-Br | H | H | H | H | H |
| 164 | 64 | I | 2 | O | 2,3,5,6-tetra-Me | H | H | H | H | H |
| 165 | 65 | I | 2 | O | 2-Et | H | H | H | H | H |
| 166 | 66 | I | 3 | O | H | H | H | H | H | H |
| 167 | 67 | I | 4 | O | 2-OH | H | H | H | H | H |
| 168 | 68 | I | 2 | O | 2-Me | 3-Me | H | H | H | H |
| 169 | 69 | I | 2 | O | 2-Me | 3-OMe | H | H | H | H |
| 170 | 70 | I | 2 | O | 2-Me | 2-OMe | H | H | H | H |
| 171 | 71 | I | 2 | O | 2-t-BuO | H | H | H | H | H |
| 172 | 72 | I | 2 | O | 2-CF₃ | 2-Cl | H | H | H | H |
| 173 | 73 | I | 2 | O | 2-Me | 2-Cl | H | COOEt | H | H |
| 174 | 74 | I | 2 | O | 2,6-di-Me, 4-OMe | 2-Cl | H | H | H | H |
| 175 | 75 | I | 4 | O | 2-Me | 2-Cl | H | H | H | H |
| 176 | 76 | 1 | 2 | O | 2-O-allyl | H | H | H | H | H |
| 177 | 77 | I | 2 | O | 2-Me | 2-Cl | 4-Me | H | H | H |
| 178 | 78 | I | 2 | O | 2-OMe | 2-Cl | H | H | H | H |
| 179 | 79 | I | 2 | O | 2-OH, 3-allyl | H | H | H | H | H |
| 180 | 80 | I | 2 | O | 2,4,5-tri-F | 2-Cl | H | H | H | H |
| 181 | 81 | I | 2 | O | 2-Me | 2-Cl | H | COCF₃ | H | H |
| 182 | 82 | I | 2 | O | 2,6-di-Me | 2-Cl | H | H | H | H |
| 183 | 83 | I | 2 | O | 2-Me,4-F | 2-Cl | H | H | H | H |
| 184 | 84 | i | 2 | O | 2-Me | 2-Cl | H | CONMe₂ | H | H |
| 185 | 85 | I | 2 | O | H | H | H | n-butyl | H | H |
| 186 | 86 | I | 2 | O | H | H | H | COCF₃ | H | COCF₃ |
| 187 | 87 | I | 2 | O | H | H | H | COCF₃ | H | H |
| 188 | 88 | I | 2 | O | H | H | H | CONHpropyl | H | H |
| 189 | 89 | I | 2 | O | H | H | H | COH | H | H |

TABLE 4

| Comp. No. | Prep. No. | General formula | Position of $NO_2$ | X | $R_1$ | $R_2$ | $R_3$ | $R_6$ |
|---|---|---|---|---|---|---|---|---|
| 201 | 1 | II | 2 | O | H | H | H | H |
| 202 | 2 | II | 4 | O | H | H | H | H |
| 203 | 3 | II | 2 | O | H | H | 4-Me | H |
| 204 | 4 | II | 2 | O | H | H | 4-$CF_3$ | H |
| 205 | 5 | II | 2 | O | H | H | 4-COOH | H |
| 206 | 6 | II | 4 | O | H | H | 2-CN | H |
| 207 | 7 | II | 4 | O | H | H | 2-COOH | H |
| 208 | 8 | II | 4 | O | H | H | 2-Me | H |
| 209 | 9 | II | 2 | O | 2-F | H | H | H |
| 210 | 10 | II | 2 | O | 4-F | H | H | H |
| 211 | 11 | II | 2 | O | 4-t-Bu | H | H | H |
| 212 | 12 | II | 2 | O | 3-F | H | H | H |
| 213 | 13 | II | 2 | O | 2-Cl | H | H | H |
| 214 | 14 | II | 2 | O | 3-Cl | H | H | H |
| 215 | 15 | II | 2 | O | 2-OMe | H | H | H |
| 216 | 16 | II | 2 | O | 3-N(Me)$_2$ | H | H | H |
| 217 | 17 | II | 2 | O | 4-Cl | H | H | H |
| 218 | 18 | II | 2 | O | 3-Me | H | H | H |
| 219 | 19 | II | 4 | O | H | 3-$NO_2$ | H | H |
| 220 | 20 | II | 2 | O | 4-n-pentyl | H | H | H |
| 221 | 21 | II | 2 | O | 4-Cl; 2-SCH(Me)$_2$ | H | H | H |
| 222 | 22 | II | 2 | O | 4-CF3 | H | H | H |
| 223 | 23 | II | 2 | O | 3,4,5-tri-OMe | H | H | H |
| 224 | 24 | II | 2 | O | H | H | H | Me |
| 225 | 25 | II | 2 | O | 2-Me | H | H | H |
| 226 | 26 | II | 2 | O | 2,4-di-Cl | H | H | H |
| 227 | 27 | II | 2 | O | 3,4-(OCH$_2$)$_2$ | H | H | H |
| 228 | 28 | II | 2 | O | 4-Cl | 2-Cl | H | H |
| 229 | 29 | II | 2 | O | 4-(1-methylbutyloxy) | H | H | H |
| 230 | 30 | II | 2 | O | 2,3-di-OMe | H | H | H |
| 231 | 31 | II | 2 | O | 3-n-BuO | H | H | H |
| 232 | 32 | II | 2 | O | 3-$CF_3$ | H | H | H |
| 233 | 33 | II | 2 | O | 3,5-di-Cl | H | H | H |
| 234 | 34 | II | 2 | O | 4-OCH$_2$Ph | H | H | H |
| 235 | 35 | II | 2 | O | 4-OEt | H | H | H |
| 236 | 36 | II | 4 | O | H | H | 2-Cl | H |
| 237 | 37 | II | 2 | O | 3-OMe, 4-Me | H | H | H |
| 238 | 38 | II | 2 | O | H | 2-Cl | H | H |
| 239 | 39 | II | 2 | O | 4-OMe | H | H | H |
| 240 | 40 | II | 2 | O | H | 3-Me | H | H |
| 241 | 41 | II | 2 | O | 2-Ph | H | H | H |
| 242 | 42 | II | 2 | O | 3-Ph | H | H | H |
| 243 | 43 | II | 2 | O | 2-Me | 2-Cl | H | H |
| 244 | 44 | II | 2 | O | 3-CN | H | H | H |
| 245 | 45 | II | 2 | O | 4-Ph | 14 | H | H |
| 246 | 46 | II | 4 | O | 2-Me | H | H | H |
| 247 | 47 | II | 2 | O | 2-OH | H | H | H |
| 248 | 48 | II | 2 | O | 2-Et | H | H | H |
| 249 | 49 | II | 2 | O | 2-CH$_2$OPh | H | H | H |
| 250 | 50 | II | 2 | O | 2-Br | H | H | H |
| 251 | 51 | II | 2 | O | 2,3,5,6-tetra-Me | H | H | H |
| 252 | 52 | II | 2 | O | 2-Me | 3-OMe | H | H |
| 253 | 53 | II | 2 | O | 2-Me | 3-Me | H | H |
| 254 | 54 | II | 2 | O | 2-O-allyl | H | H | H |
| 255 | 55 | II | 2 | O | 2-Me | 2-OMe | H | H |
| 256 | 56 | II | 2 | O | 2-t-BuO | H | H | H |
| 257 | 57 | II | 2 | O | 2-$CF_3$ | 2-Cl | H | H |
| 258 | 58 | II | 2 | O | 3-allyl, 2-OH | H | H | H |
| 259 | 59 | II | 2 | O | 2,6-di-Me, 4-OMe | 2-Cl | H | H |
| 260 | 60 | II | 2 | O | 2-Me | 2-Cl | 4-Me | H |
| 261 | 61 | II | 4 | O | 2-Me | 2-Cl | H | H |
| 262 | 62 | II | 2 | O | 2-OMe | 2-Cl | H | H |
| 263 | 63 | II | 2 | O | 2,4,5-tri-F | 2-Cl | H | H |
| 264 | 64 | II | 2 | O | 2,6-di-Me | 2-Cl | H | H |
| 265 | 65 | II | 2 | O | 2-Me,4-F | 2-Cl | H | H |
| 266 | 66 | II | 2 | O | H | H | 5-OH | H |

General Procedure 1: Coupling of Compounds of the General Formula III with Compounds of the General Formula IVa or IVb to Compounds of the General Formula II To a solution of a compound with the general formula III (50 mmol) and a compound with the general formula IVa or IVb (50 mmol) in DMSO (250 ml) was added potassium tert-butoxide (125 g, 110 mmol). The reaction mixture was stirred at room temperature for 24 hours, diluted with water (2.5 l) and acidified with vigorous stirring to pH 5–6 by the addition of acetic acid (100 ml, 3 M). The reaction mixture was cooled and stirred for 12 hours, filtered off and washed with water.

The precipitate was dried and purified by recrystallization from an appropriate solvent to give a compound of the general formula II.

General Procedure 2: Coupling of Compounds the General Formula III with Compounds of the General Formula IVa or IVb to Compounds of the General Formula II To a solution of a compound with the general formula III (10 mmol) and a compound with the general formula IVa or IVb (10 mmol) in DMSO (25 ml) was added potassium tert-butoxide (2.36 g, 21 mmol). The reaction mixture was stirred at room temperature for 40 hours, diluted with water (300 ml) and extracted with ethyl acetate (3×100 ml). The organic phase was dried ($MgSO_4$), filtered and evaporated to afford the crude product. The crude product was further purified either by crystallization or flash chromatography to yield the title compound.

General Procedure 3: Reduction of Compounds of the General Formula II to the Corresponding Compounds of the General Formula I by Treatment with Hydrazine Hydrate To a suspension of a compound with the general formula II (30 mmol) in ethanol (300 ml) was added, under argon, hydrazine hydrate (99%, 3.0 ml, 60 mmol) and 10% palladium on carbon (3.0 g). The reaction mixture was stirred at room temperature for 24 hours. The mixture was filtered through Celite® and treated with water (1.0 l). The precipitate that forms was filtered off, washed with water. The precipitate was dried and purified by recrystallization from an appropriate solvent to give a compound of the general formula I.

General Procedure 4: Reduction of Compounds of the General Formula II to the Corresponding Compounds of the General Formula I by Treatment with Stannous Chloride Dihydrate A mixture of a compound with the general formula II (5 mmol) and stannous chloride dihydrate (5.64 g, 25 mmol) in absolute ethanol (50 ml) was heated to 70° C. under argon. After 1 hour the starting material has disappeared and the solution was allowed to cool to room temperature and then poured into ice. The pH was made slightly alkaline by the addition of saturated sodium bicarbonate (50 ml) before being extracted with ethyl acetate (3×100 ml). The organic phase was dried ($MgSO_4$), filtered and evaporated to afford the crude product. The crude product was further purified either by crystallization or flash chromatography to yield the title compound.

General Procedure 5: Sulfonation of Compounds of the General Formula I (Exemplified by Compound 101) to the Corresponding Compounds of the General Formula I (Exemplified by Compound 123) by Treatment with Various Alkyl or Aryl Sulfonyl Chlorides To a cold (ice/water) solution of 4-(2-aminophenylamino) benzophenone (0.58 g, 2 mmol) in pyridine (10 ml) was added ethanesulfonyl chloride (0.25 ml, 2.7 mmol). The reaction mixture was warmed to room temperature. After stirring for 75 min, the reaction mixture was poured into ice water. The precipitate was filtered off, washed with water, and diethyl ether to afford the title compound.

General Procedure 6: Alkylation of Compounds of the General Formula I (Exemplified by Compound 101) to the Coresponding Compounds of the General Formula I (Exemplified by Compound 134) by Treatment with Alkyl Halogenide A mixture of 4-(2-aminophenylamino)benzophenone (0.29 g, 1 mmol), methyl iodide (0.1 ml, 1.7 mmol) and potassium carbonate (0.28 g, 2 mmol) in N,N-dimethylformamide (5 ml) was stirred at room temperature for 4 days. The reaction mixture was evaporated in vacuo. The residue was extracted with ethyl acetate (25 ml), filtered and evaporated to afford the crude product. The crude product was purified by flash chromatography using ethyl acetate/pentane 1:9 to give the title compound.

Preparation 1

4-(2-Nitrophenylamino)benzophenone (Compound 201)

General procedure 1
Starting compound III: 4-Aminobenzophenone
Starting compound IVa: 1-Fluoro-2-nitrobenzene
Purification: Crystallization from ethanol
Mp: 115–117° C.
$^1$H NMR (DMSO-$d_6$): δ7.12 (m, 1H), 7.35 (d, 2H), 7.50–7.80 (m, 9H), 8.12 (dd, 1H), 9.37 (bs, 1H)

Preparation 2

4-(2-Nitrophenylamino)benzophenone (Compound 202)

General procedure 1
Starting compound III: 4-Aminobenzophenone
Starting compound IVb: 1-Fluoro-4-nitrobenzene
Mp: 208–210° C.
$^1$H NMR (DMSO-$d_6$): δ7.31 (d, 2H), 7.37 (d, 2H), 7.53–7.77 (m, 7H), 8.18 (d, 2H), 9.76 (s, 1H)

Preparation 3

4-(4-Methyl-2-nitrophenylamino)benzophenone (Compound 203)

General procedure 1
Starting compound III: 4-Aminobenzophenone
Starting compound IVa: 4-Fluoro-3-nitrotoluene
Purification: Chromatography using ethyl acetate/pentane 3:7 as eluant
Mp: 131–133° C.
$^1$H NMR (DMSO-$d_6$): δ2.34 (s, 3H), 7.25 (d, 2H), 7.47–7.75 (m, 9H), 7.93 (bs, 1H), 9.21 (bs, 1H)

Preparation 4

4-(4-Trifluoromethyl-2-nitrophenylamino) benzophenone (Compound 204)

General procedure 1
Starting compound III: 4-Aminobenzophenone
Starting compound IVa: 2-Fluoro-5-trifluoromethyl-nitrobenzene
Mp: 139–141° C.
$^1$H NMR (DMSO-$d_6$): δ7.50–7.90 (m, 11H), 8.40 (bd, 1H), 9.82 (bs, 1H)

Preparation 5

4-(4-Benzoylphenylamino)-3-nitrobenzoic acid (Compound 205)

General procedure 1
Starting compound III: 4-Aminobenzophenone
Starting compound IVa: 4-Fluoro-3-nitrobenzoic acid
Mp: >250° C. (potassium salt)

$^1$H NMR (DMSO-d$_6$): (potassium salt) δ7.36 (d, 2H), 7.47 (d, 1H), 7.52–7.77 (m, 7H), 8.06 (dd, 1H), 8.53 (d, 1H), 9.44 (bs, 1H)

Preparation 6

2-(4-Benzoylphenylamino)-5-nitrobenzonitrile
(Compound 206)

General procedure 1
Starting compound III: 4-Aminobenzophenone
Starting compound IVb: 2-Fluoro-5-nitrobenzoenitrile
Purification: Crystallization from n-propanol
Mp: 208–210° C.
$^1$H NMR (DMSO-d$_6$): δ7.45–7.85 (m, 10H), 8.31 (dd, 1H), 8.65 (d, 1H), 9.67 (bs, 1H)

Preparation 7

2-(4-Benzoylphenylamino)-5-nitrobenzoic acid
(Compound 207)

General procedure 1
Starting compound III: 4-Aminobenzophenone
Starting compound IVb: 2-Fluoro-5-nitrobenzoic acid
Mp: 216–218° C.
$^1$H NMR (DMSO-d$_6$): δ7.45–7.90 (m, 10H), 8.26 (dd, 1H), 8.74 (d, 1H), 10.65 (bs, 1H), 14.0 (bs, 1H)

Preparation 8

4-(2-Methyl-4-nitrophenylamino)benzophenone
(Compound 208)

General procedure 1
Starting compound III: 4-Aminobenzophenone
Starting compound IVb: 2-Fluoro-5-nitrotoluene
Mp: 207–209° C.
$^1$H NMR (DMSO-d$_6$): δ2.38 (s, 3H), 7.31 (d, 2H), 7.44 (d, 1H), 7.52–7.80 (m, 7H), 8.02 (dd, 1H), 8.14 (d, 1H), 8.67 (bs, 1H)

Preparation 9

2-Fluoro-4'-(2-nitrophenylamino)benzophenone
(Compound 209)

General procedure 2
Starting compound III: 4-Amino-2'-fluorobenzophenone
Starting compound IVa: 1-Fluoro-2-nitrobenzene
Purification: Chromatography using diethyl ether/pentane 1:2 as eluant
Mp: 131–132° C.
$^1$H NMR (CDCl$_3$): δ6.94 (m, 1H), 7.17 (dd, 1H), 7.25–7.35 (m, 3H), 7.45–7.60 (m, 4H), 7.87 (m, 2H), 8.21 (dd, 1H), 9.51 (bs, 1H)

Preparation 10

4-Fluoro-4'-(2-nitrophenylamino)benzophenone
(Compound 210)

General procedure 2
Starting compound III: 4-Amino-4'-fluorobenzophenone
Starting compound IVa: 1-Fluoro-2-nitrobenzene
Purification: Crystallization from acetone/water
Mp: 148–150° C.
$^1$H NMR (CDCl$_3$): δ6.92 (m, 1H), 7.18 (m, 2H), 7.35 (d, 2H), 7.49 (m, 2H), 7.84 (m, 4H), 8.23 (dd, 1H), 9.52 (bs, 1H)

Preparation 11

4-Tert-butyl-4'-(2-nitrophenylamino)benzophenone
(Compound 211)

General procedure 2
Starting compound III: 4-Amino-4'-tert-butylbenzophenone
Starting compound IVa: 1-Fluoro-2-nitrobenzene
Purification: Crystallization from methanol
Mp: 189–194° C.
$^1$H NMR (CDCl$_3$): δ1.38 (s, 9H), 6.90 (m, 1H), 7.34 (d, 2H), 7.50 (m, 4H), 7.75 (d, 2H), 7.87 (d, 2H), 8.22 (dd, 1H), 9.53 (bs, 1H)

Preparation 12

3-Fluoro-4'-(2-nitrophenylamino)benzophenone
(Compound 212)

General procedure 2
Starting compound III: 4-Amino-3'-fluorobenzophenone
Starting compound IVa: 1-Fluoro-2-nitrobenzene
Purification: Crystallization from methanol
$^1$NMR (CDCl$_3$): δ6.94 (m, 1H), 7.25–7.65 (m, 8H), 7.86 (d, 2H), 8.23 (dd, 1H), 9.52 (s, 1H)

Preparation 13

2-Chloro-4'-(2-nitrophenylamino)benzophenone
(Compound 213)

General procedure 2
Starting compound III: 4-Amino-2'-chlorobenzophenone
Starting compound IVa: 1-Fluoro-2-nitrobenzene
Purification: Chromatography using diethyl ether/pentane 3:7 as eluant
$^1$H NMR (CDCl$_3$): δ6.95 (m, 1H), 7.25–7.57 (m, 8H), 7.83 (d, 2H), 8.22 (dd, 1H), 9.49 (bs, 1H)

Preparation 14

3-Chloro-4'-(2-nitrophenylamino)benzophenone
(Compound 214)

General procedure 2
Starting compound III: 4-Amino-3'-chlorobenzophenone
Starting compound IVa: 1-Fluoro-2-nitrobenzene
$^1$H NMR (CDCl$_3$): δ6.94 (m, 1H), 7.32–7.62 (m, 6H), 7.66 (d, 1H), 7.76 (bs, 1H), 7.86 (d, 2H), 8.23 (dd, 1H), 9.52 (s, 1H)

Preparation 15

2-Methoxy-4'-(2-nitrophenylamino)benzophenone
(Compound 215)

General procedure 2
Starting compound III: 4-Amino-2'-methoxybenzophenone
Starting compound IVa: 1-Fluoro-2-nitrobenzene
Purification: Chromatography using diethyl ether/pentane 1:2 as eluant $^1$H NMR (CDCl$_3$): δ3.76 (s, 3H), 6.94 (m, 1H), 7.05 (m, 2H), 7.27 (d, 2H), 7.36 (dd, 1H), 7.50 (m, 3H), 7.84 (d, 2H), 8.21 (dd, 1H), 9.50 (s, 1H)

Preparation 16

3-Dimethylamino4'-(2-nitrophenylamino)benzophenone (Compound 216)

General procedure 2

Starting compound III: 4-Amino-3'-(dimethylamino)benzophenone

Starting compound IVa: 1-Fluoro-2-nitrobenzene

Purification: Chromatography using ethyl acetate/pentane 1:4 as eluant $^1$H NMR (CDCl$_3$): δ3.00 (s, 6H), 6.92 (m, 2H), 7.04 (dd, 4H), 7.15 (m, 1H), 7.28 (m, 3H), 7.50 (m, 2H), 7.89 (d, 2H), 8.21 (dd, 1H), 9.52 (bs, 1H)

Preparation 17

4-Chloro-4'-(2-nitrophenylamino)benzophenone (Compound 217)

General procedure 2

Starting compound III: 4-Amino-4'-chlorobenzophenone

Starting compound IVa: 1-Fluoro-2-nitrobenzene

Purification: Crystallization from ethyl acetate/pentane 1:2

Mp: 157–1587° C.

$^1$H NMR (CDCl$_3$): δ6.93 (m, 1H), 7.35 (d, 2H), 7.50 (m, 4m), 7.75 (d, 2H), 7.84 (d, 2H), 8.23 (dd, 1H), 9.52 (s, 1H)

Preparation 18

3-Methyl -4'-(2-nitrophenylamino)benzophenone (Compound 218)

General procedure 2

Starting compound III: 4-Amino-3'-methylbenzophenone

Starting compound IVa: 1-Fluoro-2-nitrobenzene

Purification: Chromatography using ethyl acetate/pentane 1:9 as eluant

Mp: 86–87° C.

$^1$H NMR (CDCl$_3$): δ2.43 (s, 3H), 6.92 (m, 1H), 7.30–7.65 (m, 8H), 7.87 (d, 2H), 8.22 (dd, 1H), 9.52 (s, 1H)

Preparation 19

3-Nitro-4-(4-nitrophenylamino)benzophenone (Compound 219)

General procedure 1

Starting compound III: 4-Amino-3-nitrobenzophenone

Starting compound IVa: 1-fluoro-4-nitrobenzene

Purification: Crystallization from n-propanol

Mp: 199–201° C.

$^1$H NMR (DMSO-d$_6$): δ7.50–7.80 (m, 8H), 7.99 (dd, 1H), 8.25 (d, 2H), 8.44 (d, 1H), 9.98 (s, 1H)

Preparation 20

4-(2-Nitrophenylamino)-4'-pentylbenzophenone (Compound 220)

General procedure 2

Starting compound III: 4-Amino-4'-pentylbenzophenone

Starting compound IVa: 1-Fluoro-2-nitrobenzene

Purification: Crystallization from ethyl acetate

Mp: 93–95° C.

$^1$H NMR (CDCl$_3$): δ0.92 (t, 3H), 1.40 (m, 4H), 1.73 (m, 2H), 3.01 (t, 2H), 6.92 (m, 1H), 7.34 (m, 4H), 7.47 (m, 2H), 7.73 (d, 2H), 7.84 (d, 2H), 8.23 (dd, 1H), 9.52 (s, 1H)

Preparation 21

4-Chloro-2-isopropylthio-4'-(2-nitrophenylamino)benzophenone (Compound 221)

General procedure 2

Starting compound III: 4'-Amino-4-chloro-2-(isopropylthio)benzophenone

Starting compound IVa: 1-Fluoro-2-nitrobenzene

Purification: Chromatography using ethyl acetate/pentane 1:9 as eluant $^1$NMR (CDCl$_3$): δ1.25 (d, 6H), 3.40 (m, 1H), 6.94 (m, 1H), 7.27 (m, 4H), 7.50 (m, 3H), 7.79 (d, 2H), 8.21 (dd, 1H), 9.49 (bs, 1H)

Preparation 22

4-Trifluoromethyl-4'-(2-nitrophenylamino)benzophenone (Compound 222)

General procedure 2

Starting compound III: 4-Amino-4'-trifluoromethylbenzophenone

Starting compound IVa: 1-Fluoro-2-nitrobenzene

Purification: Chromatography using ethyl acetate/pentane 1:9 as eluant

Mp: 122–123° C.

$^1$H NMR (CDCl$_3$): δ6.96 (m, 1H), 7.36 (d, 2H), 7.50 (m, 2H), 7.77 (d, 2H), 7.87 (m, 4H), 8.23 (dd, 1H), 9.52 (s, 1H)

Preparation 23

3,4,5-Trimethoxy-4'-(2-nitrophenylamino)benzophenone (Compound 223)

General procedure 2

Starting compound III: 4'-Amino-3,4,5-trimethoxybenzophenone

Starting compound IVa: 1-Fluoro-2-nitrobenzene

Purification: Trituration from ethyl acetate/pentane 1:2

Mp: sublimate 180–191° C.

$^{13}$C NMR (CDCl$_3$): δ194.4, 152.9, 143.3, 142.0, 140.4, 135.7, 135.0, 133.4, 132.8, 132.0, 126.8, 120.9, 119.5, 117.2, 107.6, 61.0, 56.4

Preparation 24

4-(N-Methyl-2-nitrophenyllamino)benzophenone (Compound 224)

General procedure 6, but using 5 mmol methyl iodide

Starting compound: 201

Purification: Chromatography using ethyl acetate/pentane 1:9 as eluant $^1$H NMR (DMSO-d$_6$): δ8.09 (m, 1H), 7.87 (m, 1H), 7.68–7.57 (m, 7H), 7.52 (m, 2H), 6.65 (m, 2H), 3.34 (s,3H)

Preparation 25

2-Methyl-4'-(2-nitrophenylamino)benzonhenone (Compound 225)

General procedure 2

Starting compound III: 4-Amino-2'-methylbenzophenone

Starting compound IVa: 1-Fluoro-2-nitrobenzene

Purification: Chromatography using ethyl acetate/pentane 1:4 as eluant

Mp: 87–90° C.

$^{13}$C NMR (CDCl$_3$): δ197.0, 144.0, 140.2, 138.7, 136.5, 135.6, 135.2, 133.3, 132.1, 131.0, 130.1, 128.1, 126.8, 125.3, 120.8, 119.6, 117.4, 19.9

Preparation 26

2,4-Dichloro-4'-(2-nitrophenylamino)benzophenone (Compound 226)

General procedure 2

Starting compound III: 4'-Amino-2,4-dichlorobenzophenone

Starting compound IVa: 1-Fluoro-2-nitrobenzene

Purification: Chromatography using ethyl acetate/pentane 1:4 as eluant $^{13}$C NMR (CDCl$_3$): δ192.6, 144.9, 139.6, 137.1, 136.5, 135.6, 132.3, 132.1, 131.6, 130.0, 127.2, 126.8, 120.4, 120.1, 117.7

Preparation 27

3,4-Ethylenedioxy-4'-(2-nitrophenylamino) benzophenone (Compound 227)

General procedure 2

Starting compound III: 4'-Amino-3,4-ethylenedioxybenzophenone

Starting compound IVa: 1-Fluoro-2-nitrobenzene

Purification: Chromatography using ethyl acetate/pentane 1:2 as eluant

Mp: 145–147° C.

$^{13}$C NMR (CDCl$_3$): δ193.9, 147.6, 143.2, 142.9, 140.8, 135.7, 134.8. 133.9, 131.9, 131.1, 126.8, 124.2, 121.2, 119.6, 119.2, 117.1, 117.0, 64.7, 64.2

Preparation 28

2,4'-Dichloro-4-(2-nitrophenylamino)benzophenone (Compound 228)

General procedure 2

Starting compound III: 4-Amino-2,4'-dichlorobenzophenone

Starting compound IVa: 1-Fluoro-2-nitrobenzene

Purification: Chromatography using ethyl acetate/pentane 1:4 as eluant

Mp: 140–142° C.

$^{13}$C NMR (CDCl$_3$): δ193.3, 142.5, 140.2, 140.2, 135.8, 135.2, 135.1, 133.6, 133.2, 131.4, 131.1, 129.0, 126.9, 123.0, 120.0, 119.7, 117.0

Preparation 29

4-(2-Nitrophenylamino)-4'-(1-methylbutyloxy) benzophenone (Compound 229)

General procedure 2

Starting compound III: 4-Amino-4'-(1-1-methylbutyloxy)benzophenone

Starting compound IVa: 1-Fluoro-2-nitrobenzene

Purification: Chromatography using ethyl acetate/pentane 1:4 as eluant $^{13}$C NMR (CDCl$_3$): δ194.1, 162.1, 142.7, 140.9, 135.7, 134.7, 134.3, 132.4, 131.8, 129.8, 126.8, 121.3, 119.1, 117.0, 115.0, 73.9, 38.5, 19.7, 18.7, 14.0

Preparation 30

2,3-Dimethoxy-4'-(2-nitrophenylamino) benzophenone (Compound 230)

General procedure 2

Starting compound III: 4'-Amino-2,3-dimethioxybenzophenone

Starting compound IVa: 1-Fluoro-2-nitrobenzene

Purification: Chromatography using diethyl ether/pentane 1:1 as eluant $^{13}$C NMR (CDCl$_3$): δ194.6, 152.8, 146.7, 144.0, 140.2, 135.6, 135.1, 134.2, 133.1, 132.0, 126.8, 124.2, 120.7, 120.3, 119.5, 117.4, 114.2, 61.8, 56.0

Preparation 31

3-Butoxy-4'-(2-nitrophenylamino)benzophenone (Compound 231)

General procedure 2

Starting compound III: 4-Amino-3'-butoxybenzophenone

Starting compound IVa: 1-Fluoro-2-nitrobenzene

Purification: Chromatography using diethyl ether/pentane 1:4 as eluant $^{13}$C NMR (CDCl$_3$): δ195.1, 159.2, 143.4, 140.5, 139.0, 135.7, 135.0, 133.3, 132.1, 129.2, 126.8, 122.3, 121.0, 119.4, 119.0, 117.2, 115.0, 68.0, 31.3, 19.2, 13.9

Preparation 32

4-(2-Nitrophenylamino)-3'-(trifluoromethyl) benzophenone (Compound 232)

General procedure 2

Starting compound III: 4-Amino-3,-(trifluoromethyl)benzophenone

Starting compound IVa: 1-Fluoro-2-nitrobenzene

Purification: Chromatography using ethyl acetate/pentane 1:2 as eluant followed by trituration from diethyl ether $^{13}$C NMR (CDCl$_3$): δ193.7, 144.1, 140.0, 138.6, 135.7, 135.4, 132.9, 132.2, 132.1, 131.0, 129.0, 128.7, 126.9, 126.5, 123.7, 120.8, 119.8, 117.4

Preparation 33

3,5-Dichloro-4'-(2-nitrophenylamino)benzophenone (Compound 233)

General procedure 2

Starting compound III: 4'-Amino-3,5-dichlorobenzophenone

Starting compound IVa: 1-Fluoro-2-nitrobenzene

Purification: Chromatography using diethyl ether/pentane 1:2 as eluant $^{13}$C NMR (CDCl$_3$): δ192.2, 144.4, 140.5, 139.8, 135.6, 135.5, 135.3, 132.2, 131.9, 131.6, 127.9, 126.9, 120.6, 119.9, 117.5

Preparation 34

4-Benzyloxy-4'-(2-nitrophenylamino)benzophenone (Compound 234)

General procedure 2

Starting compound III: 4-Amino-4'-benzyloxybenzophenone

Starting compound IVa: 1-Fluoro-2-nitrobenzene
Purification: Chromatography using ethyl acetate/pentane 1:2 as eluant
$^{13}$C NMR (CDCl$_3$): δ193.9, 162.1, 142.6, 140.6, 136.0, 135.4, 134.6, 133.8, 132.1, 131.6, 130.3, 128.5, 128.0, 127.3, 126.6, 121.0, 119.0, 116.8, 114.3, 70.0

Preparation 35

4-Ethoxy-4'-(2-nitrophenylamino)benzophenone (Compound 235)

General procedure 2
Starting compound III: 4-Amino-4'-ethoxybenzophenone
Starting compound IVa: 1-Fluoro-2-nitrobenzene
Purification: Trituration from diethyl ether/pentane 1:2
$^{13}$C NMR (CDCl$_3$): δ194.1, 162.6, 142.8, 140.8, 135.7, 134.8, 134.2, 132.4, 131.8, 130.0, 126.8, 121.3, 119.1, 117.0, 114.1, 63.8, 14.7

Preparation 36

4-(2-Chloro4-nitrophenylamino)benzophenone (Compound 236)

General procedure 1
Starting compound III: 4-Aminobenzophenone
Starting compound IVb: 1-Chloro-2-fluoro-5-nitrobenzene
Purification: Trituration from ethanol
Mp: 214–218° C.
$^1$H NMR (DMSO-d$_6$): δ9.08 (bs, 1H), 8.33 (d, 1H), 8.11 (dd, 1H), 7.83–7.63 (m, 5H), 7.57 (m, 2H), 7.50 (d, 1H), 7.43 (d, 2H)

Preparation 37

3-Methoxy-4-methyl-4'-(2-nitrophenylamino)benzophenone (Compound 237)

General procedure 2
Starting compound III: 4'-Amino-3-methoxy-4-methylbenzophenone
Starting compound IVa: 1-Fluoro-2-nitrobenzene
Purification: Trituration from methanol
$^{13}$C NMR (CDCl$_3$): δ195.2, 157.9, 143.2, 140.6, 136.5, 135.7, 134.9, 133.7, 132.3, 132.0, 130.0, 126.8, 123.0, 121.1, 119.3, 117.1, 110.5, 55.5, 16.5

Preparation 38

2-Chloro-4-(2-nitrophenylamino)benzophenone (Compound 238)

General procedure 2
Starting compound III: 4-Amino-3-chlorobenzophenone
Starting compound IVa: 1-Fluoro-2-nitrobenzene
Purification: Chromatography using ethyl acetate/pentane 1:4 as eluant followed by crystallization from methanol
$^{13}$C NMR (CDCl$_3$): δ194.5, 142.2, 140.5, 136.8, 135.8, 134.9, 134.2, 133.6, 133.2, 131.1, 130.1, 128.6, 126.9, 123.2, 120.1, 119.5, 116.9

Preparation 39

4-Methoxy-4'-(2-nitrophenylamino)benzophenone (Compound 239)

General procedure 2
Starting compound III: 4-Amino-4'-methoxy benzophenone
Starting compound IVa: 1-Fluoro-2-nitrobenzene
Purification: Crystallization from ethyl acetate
$^{13}$C NMR (CDCl$_3$): δ194.1, 163.2, 142.8, 140.8, 135.7, 134.8, 134.1, 132.4, 131.8, 130.3, 126.8, 121.3, 119.2, 117.0, 113.6, 55.5

Preparation 40

3-Methyl-4-(2-nitrophenylamino)benzophenone (Compound 240)

General procedure 2
Starting compound III: 4-Amino-3-methylbenzophenone
Starting compound IVa: 1-Fluoro-2-nitrobenzene
Purification: Crystallization from ethanol
$^{13}$C NMR (CDCl$_3$): δ5.6, 141.7, 141.4, 137.8, 135.7, 134.3, 134.1, 133.4, 132.3, 131.7, 129.9, 129.4, 128.3, 126.8, 121.9, 118.7, 116.8, 18.1

Preparation 41

4-(2-Nitrophenylamino)-2'-phenylbenzophenone (Compound 241)

General procedure 2
Starting compound III: 4-Amino-2'-phenylbenzophenone
Starting compound IVa: 1-Fluoro-2-nitrobenzene
Purification: Chromatography using ethyl acetate/pentane 1:4 as eluant
$^{13}$C NMR (CDCl$_3$): δ197.2, 143.4, 141.0, 140.4, 140.2, 138.9, 135.5, 135.0, 133.3, 131.8, 130.4, 130.0, 129.1, 128.7, 128.3, 127.4, 127.2, 126.8, 120.7, 119.4, 117.2

Preparation 42

4-(2-Nitrophenylamino)-3'-phenylbenzophenone (Compound 242)

General procedure 2
Starting compound III: 4-Amino-3'-phenylbenzophenone
Starting compound IVa: 1-Fluoro-2-nitrobenzene
Purification: Crystallization from a mixture of chloroform/methanol
Mp: 142–145° C.
$^{13}$C NMR (CDCl$_3$): δ195.2, 143.5, 141.4, 140.4, 140.2, 138.4, 135.6, 135.0, 133.1, 132.2, 130.9, 128.9, 128.8, 128.6, 128.4, 127.8, 127.2, 126.8, 120.9, 119.5, 117.2

Preparation 43

2-Chloro-2'-methyl-4-(2-nitrophenylamino)benzophenone (Compound 243)

General procedure 2
Starting compound III: 4-Amino-2-chloro-2'-methylbenzophenone
Starting compound IVa: 1-Fluoro-2-nitrobenzene
Purification: Chromatography using ethyl acetate/pentane 1:9 followed by methylene chloride/pentane 2:1 as eluant
$^{13}$C NMR (CDCl$_3$): δ196.4, 142.7, 140.1, 139.0, 137.6, 135.8, 135.1, 134.7, 134.0, 132.2, 131.8, 131.7, 130.6, 126.9, 125.6, 123.0, 119.8, 119.7, 117.1, 20.9

Preparation 44

3-Cyano-4'-(2-nitrophenylamino)benzophenone (Compound 244)

General procedure 2
Starting compound III: 4-Amino-3'-cyanobenzophenone

Starting compound IVa: 1-Fluoro-2-nitrobenzene

Purification: Chromatography using ethyl acetate/pentane 1:3 as eluant $^{13}$C NMR (CDCl$_3$): δ192.8, 144.4, 139.8, 138.9, 135.7, 135.5, 135.2, 133.6, 133.2, 132.2, 131.6, 129.5, 126.9, 120.7, 120.0, 118.0, 117.5, 112.8

Preparation 45

4-(2-Nitrophenylamino)-4'-phenylbenzophenone (Compound 245)

General procedure 2

Starting compound III: 4-Amino-4'-phenylbenzophenone

Starting compound IVa: 1-Fluoro-2-nitrobenzene

Purification: Trituration from diethyl ether followed by chromatography using ethyl acetate/pentane 1:8 as eluant $^{13}$C NMR (DMSO-d$_6$): δ193.7, 145.4, 143.6, 139.0, 138.0, 137.6, 136.4, 135.4, 131.7, 130.5, 130.0, 129.0, 128.2, 126.9, 126.6, 126.1, 121.2, 120.4, 118.6

Preparation 46

2-Methyl-4'-(4-nitrophenylamino)benzophenone (Compound 246)

General procedure 2

Starting compound III: 4-Amino-2'-methylbenzophenone

Starting compound IVb: 1-Fluoro-4-nitrobenzene

Purification: Chromatography using ethyl acetate/pentane 1:4 followed by 1:2 as eluant $^{13}$C NMR (CDCl$_3$): δ197.3, 147.8, 145.2, 141.2, 138.9, 136.3, 132.4, 132.0, 131.0, 130.1, 128.0, 126.0, 125.3, 118.0, 116.2, 19.8

Preparation 47

2-Hydroxy-4'-(2-nitrophenylamino)benzophenone (Compound 247)

To a cooled (−78° C.) solution of 2-Methoxy-4'-(2-nitrophenylamino)-benzophenone (Compound 215, 0.35 g, 1 mmol) in methylene chloride (10 ml), under argon, was added boron tribromide (0.1 ml, 1 mmol) under stirring. The reaction mixture was allowed to come to room temperature. After stirring for 3 h, the reaction mixture was poured into saturated sodium bicarbonate (50 ml) before being extracted with ethyl acetate (2×50 ml). The organic phase was dried (MgSO$_4$), filtered and evaporated to afford the title compound.

Mp: 189–193° C.

$^{13}$C NMR (CDCl$_3$): δ199.8, 163.1, 143.1, 140.5, 136.2, 135.7, 135.0, 133.6, 133.2, 131.4, 126.9, 121.2, 119.4, 119.2, 118.7, 118.5, 117.1

Preparation 48

2-Ethyl-4'-(2-nitrophenylamino)benzophenone (Compound 248)

General procedure 2

Starting compound III: 4-Amino-2'-ethylbenzophenone

Starting compound IVa: 1-Fluoro-2-nitrobenzene

Purification: Chromatography using diethyl ether/pentane 1:4 as eluant $^{13}$C NMR (CDCl$_3$): δ197.1, 144.1, 142.8, 140.1, 138.5, 135.6, 135.2, 133.4, 132.2, 130.2, 129.4, 128.0, 126.8, 125.2, 120.7, 119.6, 117.4, 26.4, 15.9

Preparation 49

4-(2-Nitrophenylamino)-2'-(phenoxymethyl)benzophenone (Compound 2 49)

General procedure 2

Starting compound III: 4-Amino-2'-phenoxymethyl)benzophenone

Starting compound IVa: 1-Fluoro-2-nitrobenzene

Purification: Chromatography using ethyl acetate/pentane 1:4 as eluant $^{13}$C NMR (CDCl$_3$): δ196.1, 158.4, 144.0, 140.2, 137.7, 136.7, 135.6, 135.2, 133.1, 132.2, 130.6, 129.4, 128.7, 128.6, 127.3, 126.8, 121.0, 120.7, 119.6, 117.4, 114.7, 67.5

Preparation 50

2-Bromo-4'-(2-nitrophenylamino)benzophenone (Compound 250)

General procedure 2

Starting compound III: 4-Amino-2'-bromobenzophenone

Starting compound IVa: 1-Fluoro-2-nitrobenzene

Purification: Chromatography using ethyl acetate/pentane 1:4 as eluant $^{13}$C NMR (CDCl$_3$): δ194.2, 144.6, 140.8, 139.8, 135.6, 135.5, 133.2, 132.3, 131.6, 131.1, 128.9, 127.3, 126.8, 120.5, 119.9, 119.5, 117.6

Preparation 51

2,3,5,6-Tetramethyl-4'-(2-nitrophenoylamino)benzophenone (Compound 251)

General procedure 2

Starting compound III: 4'-Amino-2,3,5,6-tetramethylbenzophenone

Starting compound IVa: 1-Fluoro-2-nitrobenzene

Purification: Chromatography using methylene chloride/pentane 1:2 followed by 1:1 as eluant Mp: 211–213° C.

$^{13}$C NMR (CDCl$_3$): δ200.0, 144.3, 140.0, 139.9, 135.6, 135.3, 134.2, 133.2, 131.8, 131.5, 129.7, 126.8, 120.8, 119.7, 117.5, 19.5, 16.3

Preparation 52

3-Methoxy-2'-methyl-4-(2-nitrophenylamino)benzophenone (Compound 252)

General procedure 2

Starting compound III: 4-Amino-3-methoxy-2'-methylbenzophenone

Starting compound IVa: 1-Fluoro-2-nitrobenzene

Purification: Chromatography using methylene chloride/pentane 2:3 as eluant $^{13}$C NMR (CDCl$_3$): δ197.1, 150.2, 139.2, 138.9, 136.3, 136.1, 135.3, 134.3, 132.5, 130.9, 130.0, 128.0, 126.8, 125.2, 119.7, 117.8, 116.6, 111.2, 56.1, 19.8

Preparation 53

2', 3-Dimethyl-4-(2-nitrophenylamino)benzophenone (Compound 253)

General procedure 2

Starting compound III: 4-Amino-2',3-dimethylbenzophenone

Starting compound IVa: 1-Fluoro-2-nitrobenzene

Purification: Chromatography using ethyl acetate/pentane 1:9 as eluant $^{13}$C NMR (CDCl$_3$): δ197.5, 142.4, 141.0, 138.8, 136.5, 135.7, 134.6, 134.0, 133.3, 131.3, 131.0, 130.1, 129.5, 128.2, 126.8, 125.2, 121.3, 119.0, 117.0, 19.9, 18.0

Preparation 54

2-Allyloxy-4'-(2-nitrophenylamino)benzophenone (Compound 254)

General procedure 2

Starting compound III: 2-Allyloxy-4'-aminobenzophenone

Starting compound IVa: 1-Fluoro-2-nitrobenzene

Purification: Chromatography using ethyl acetate/pentane 1:9 as eluant $^{13}$C NMR (CDCl$_3$): δ195.0, 156.2, 143.5, 140.6, 135.6, 135.0, 134.0, 132.5, 131.9, 131.7, 129.7, 129.3, 126.8, 120.9, 119.3, 117.2, 116.9, 112.8, 69.0

Preparation 55

2-Methoxy-2'-methyl-4-(2-nitrophenylamino)benzophenone (Compound 255)

General procedure 2

Starting compound III: 4-Amino-2-methoxy-2'-methylbenzophenone

Starting compound IVa: 1-Fluoro-2-nitrobenzene

Purification: Chromatography using ethyl acetate/pentane 1:4 as eluant $^{13}$C NMR (CDCl$_3$): δ196.9, 160.2, 144.0, 140.8, 139.9, 137.4, 135.6, 134.8, 132.9, 131.1, 130.5, 129.3, 126.8, 125.4, 125.2, 119.2, 117.3, 113.5, 105.6, 55.9, 20.5

Preparation 56

2-Tert-butoxy-4'-(2-nitrophenylamino)benzophenone (Compound 256)

General procedure 2

Starting compound III: 4-Amino-2'-tert-butoxybenzophenone

Starting compound IVa: 1-Fluoro-2-nitrobenzene

Purification: Chromatography using ethyl acetate/pentane 1:10 as eluant $^{13}$C NMR (CDCl$_3$): δ196.1, 153.6, 143.4, 140.6, 135.6, 134.9, 134.8, 134.2, 131.8, 131.3, 129.7, 126.8, 123.0, 122.8, 120.9, 119.2, 117.2, 80.3, 28.8

Preparation 57

2-Chloro-4-(2-nitrophenylamino)-2'-(trifluoromethyl)benzophenone (Compound 257)

General procedure 2

Starting compound III: 4-Amino-2-chloro-2'-(trifluoromethyl)benzophenone

Starting compound IVa: 1-Fluoro-2-nitrobenzene

Purification: Chromatography using ethyl acetate/pentane 1:4 as eluant

Mp: 125–127° C.

$^{13}$C NMR (CDCl$_3$): δ193.0, 144.4, 139.2, 135.8, 135.7, 134.3, 131.6, 131.1, 130.6, 128.8, 128.3, 127.0, 126.9, 123.6, 122.5, 120.5, 118.5, 117.8

Preparation 58

3-Allyl-2-hydroxy-4'-(2-nitrophenylamino)benzophenone (Compound 258)

2-Allyloxy-4'-(2-nitrophenylamino)benzophenone (Compound 254, 1.57 g, 4.2 mmol) was heated to 220° C. under argon. After 4 h the reaction mixture was cooled to room temperature. The crude product was further purified by chromatography using ethyl acetate/pentane 1:8 as eluant to afford the title compound.

$^{13}$C NMR (CDCl$_3$): δ200.1, 161.1, 143.0, 140.6, 136.3, 136.1, 135.7, 135.0, 133.8, 131.4, 129.5, 126.9, 121.2, 119.4, 118.7, 118.2, 117.1, 116.1, 33.6

Preparation 59

2'-Chloro-4-methoxy-2,6-dimethyl-4'-(2-nitrophenylamino)benzophenone (Compound 259)

General procedure 2

Starting compound III: 4'-Amino-2'-chloro-4-methoxy-2,6-dimethylbenzophenone

Starting compound IVa: 1-Fluoro-2-nitrobenzene

Purification: Chromatography using ethyl acetate/pentane 1:9 followed by 1:4 as eluant $^{13}$C NMR (CDCl$_3$): δ197.2, 160.1, 143.7, 139.5, 137.2, 135.7, 135.6, 135.2, 133.6, 133.0, 126.9, 123.0, 120.2, 118.9, 117.6, 113.4, 55.2, 20.2

Preparation 60

2-Chloro-2'-methy-4-(2-nitro-4-methylphenylamino)benzophenone (Compound 260)

General procedure 2

Starting compound III: 4-Amino-2-chloro-2'-methylbenzophenone

Starting compound IVa: 1-Fluoro-4-methyl-2-nitrobenzene

Purification: Chromatography using ethyl acetate/pentane 1:9 followed by 1:4 as eluant $^{13}$C NMR (CDCl$_3$): δ196.4, 143.3, 138.8, 137.8, 137.5, 136.9, 135.4, 134.1, 134.0, 132.3, 131.7, 131.6, 130.5, 130.1, 126.3, 125.5, 122.2, 118.8, 117.6, 20.8, 20.3

Preparation 61

2-Chloro-2'-methyl-4-(4-nitrophenylamino)benzophenone (Compound 261)

General procedure 2

Starting compound III: 4-Amino-2-chloro-2'-methylbenzophenone

Starting compound IVb: 1-Fluoro-4-nitrobenzene

Purification: Chromatography using ethyl acetate/pentane 1:4 as eluant $^{13}$C NMR (DMSO-d$_6$): δ148.4, 144.7, 144.7, 139.9, 138.0, 137.4, 132.7, 132.7, 131.6, 131.5, 131.2, 129.8, 126.0, 125.9, 119.3, 116.5, 116.0, 20.2

Preparation 62

2-Chloro-2'-methoxy-4-(2-nitrophenylamino)benzophenone (Compound 262)

General procedure 2

Starting compound III: 4-Amino-2-chloro-2'-methoxybenzophenone

Starting compound IVa: 1-Fluoro-2-nitrobenzene

Purification: Chromatography using methylene chloride/pentane 3:1 as eluant

Mp: 111–114° C.

$^{13}$C NMR (CDCl$_3$): δEO 193.6, 158.8, 142.1, 140.5, 135.9, 135.8, 134.9, 133.9, 133.5, 131.7, 131.1, 128.3, 126.8, 123.0, 120.8, 119.9, 119.5, 117.0, 111.8, 55.8

Preparation 63

2'-Chloro-2,4,5-trifluoro-4'-(2-nitrophenylamino)benzophenone (Compound 263)

General procedure 2

Starting compound III: 4'-Amino-2-chloro-2,4,5-trifluorobenzophenone

Starting compound IVa: 1-Fluoro-2-nitrobenzene

Purification: Chromatography using ethyl acetate/pentane 1:8 as eluant $^3$C NMR (CDCl$_3$): δ185.1, 155.2, 147.9, 147.1, 144.8, 138.9, 136.1, 135.7, 135.4, 133.6, 131.4, 126.9, 122.1, 120.7, 119.9, 119.4, 118.6, 118.0, 111.6

Preparation 64

2-Chloro-2',6'-dimethyl-4-(2-nitrophenylamino)benzophenone (Compound 264)

General procedure 2

Starting compound III: 4-Amino-2-chloro-2',6'-dimethylbenzophenone

Starting compound IVa: 1-Fluoro-2-nitrobenzene

Purification: Chromatography using ethyl acetate/pentane 1:9 as eluant $^{13}$C NMR (CDCl$_3$): δ197.3, 144.1, 140.3, 139.2, 135.8, 135.7, 135.6, 134.6, 134.0, 131.6, 129.2, 127.9, 126.9, 123.0, 120.4, 118.6, 117.8, 19.6

Preparation 65

2-Chloro-4'-fluoro-2'-methyl-4-(2-nitrophenylamino)benzophenone (Compound 265)

General procedure 2

Starting compound III: 4-Amino-2-chloro-4'-fluoro-2'-methylbenzophenone

Starting compound IVa: 1-Fluoro-2-nitrobenzene

Purification: Chromatography using ethyl acetate/pentane 1:10 as eluant $^{13}$C NMR (CDCl$_3$): δ195.0, 1624.4, 142.9, 142.8, 140.1, 135.8, 135.2, 134.7, 133.8, 133.8, 133.4, 131.9, 126.9, 123.0, 119.8, 119.7, 118.7, 117.1, 112.6, 21.2

Preparation 66

4-(5-Hydroxy-2-nitrophenylamino)benzophenone (Compound 266)

General procedure 1

Starting compound III: 4-Aminobenzophenone

Starting compound IVa: 3-Fluoro-4-nitrophenol

Purification: Trituration from ethanol

Mp: 235–238° C.

$^1$H NMR (DMSO-d$_6$): δ10.94 (bs, 1H), 9.64 (s, 1H), 8.10 (d, 1H), 7.84–7.63 (m, 5H), 7.57 (m, 2H), 7.47 (m, 2H), 6.82 (d, 1H), 6.47 (dd, 1H)

EXAMPLE 1

4-(2-Aminophenylamino)benzophenone (Compound 101)

General procedure 3

Starting compound II: 201

Mp: 115–116° C.

$^1$H NMR (CDCl$_3$): δ3.67 (bs, 2H), 5.74 (bs, 1H), 6.69 (d, 2H), 6.75–6.85 (m, 2H), 7.05–7.16 (m, 2H), 7.40–7.60 (m, 3H), 7.70–7.80 (m, 4H)

EXAMPLE 2

4-(4-Aminophenylamino)benzophenone (Compound 102)

General procedure 3

Starting compound II: 202

Mp: 152–154° C.

$^1$H NMR (DMSO-d$_6$): δ4.98 (bs, 2H), 6.58 (d, 2H), 6.79 (d, 2H), 6.90 (d, 2H), 7.50–7.65 (m, 7H), 8.41 (bs, 1H)

EXAMPLE 3

4-(2-Amino-4-methylphenylamino)benzophenone (Compound 103)

General procedure 3

Starting compound II: 203

Mp: 153–155° C.

$^1$H NMR (DMSO-d$_6$): δ2.19 (s, 3H), 4.78 (bs, 2H), 6.40 (dd, 1H), 6.60 (bs, 1H), 6.67 (d, 2H), 6.90 (d, 1H), 7.45–7.65 (m, 7H), 7.98 (bs, 1H)

EXAMPLE 4

4-(2-Amino-4-trifluoromethylphenylamino)benzophenone (Compound 104)

General procedure 3

Starting compound II: 204

Mp: 184–186° C.

$^1$H NMR (DMSO-d$_6$): δ5.37 (bs, 2H), 6.88 (m, 3H), 7.09 (bd, 1H), 7.27 (d, 1H), 7.50–7.70 (m, 7H), 8.20 (bs, 1H)

EXAMPLE 5

3-Amino-4-(4-benzoylphenylamino)benzoic acid (Compound 105)

General procedure 3

Starting compound II: 205

Purification: Crystallization from a mixture of water and acetic acid

Mp: 205–207° C.

$^1$H NMR (DMSO-d$_6$): δ5.17 (b, 2H), 6.92 (d, 2H), 7.19 (m, 2H) 7.43 (bs, 1H), 7.50–7.65 (m, 8H), 8.23 (bs, 1H)

EXAMPLE 6

5-Amino-2-(4-benzoylphenylamino)benzonitrile (Compound 106)

General procedure 3

Starting compound II: 206

Mp: 168–170° C.

¹H NMR (DMSO-d₆): δ5.56 (bs, 2H), 6.75 (d, 2H), 6.91 (m, 2H), 7.14 (m, 1H), 7.50–7.70 (m, 7H), 8.63 (bs, 1H)

EXAMPLE 7

5-Amino-2-(4-benzoylphenylamino)benzoic acid (Compound 107)

General procedure 3
Starting compound II: 207
Purification: Crystallization from ethanol
Mp: 222–223° C.
¹H NMR (DMSO-d₆): δ6.81 (dd, 1H), 6.97 (d, 2H), 7.18 (m, 2H), 7.50–7.70 (m, 7H), 7.60 (b, 3H), 8.86 (bs, 1H)

EXAMPLE 8

4-(4-Amino-2-methylphenylamino)benzophenone (Compound 108)

General procedure 3
Starting compound II: 208
Mp: 140–142° C.
¹H NMR (DMSO-d₆): δ2.03 (s, 3H), 4.99 (bs, 2H), 6.43 (dd, 1H), 6.50 (m, 1H), 6.56 (d, 2H), 6.84 (d, 1H), 7.45–7.65 (m, 7H), 8.07 (s, 1H)

EXAMPLE 9

4-(2-Aminophenylamino)-2'-fluorobenzophenone (Compound 109)

General procedure 4
Starting compound II: 209
Mp: 153–154° C.
¹H NMR (CDCl₃): δ3.83 (bs, 2H), 5.74 (bs, 1H), 6.68 (d, 2H), 6.78 (m, 2H), 7.05–7.25 (m, 4H), 7.45 (m, 2H), 7.72 (d, 2H)

EXAMPLE 10

4-(2-Aminophenylamino)-4'-fluorobenzophenone (Compound 110)

General procedure 4
Starting compound II: 210
Purification: Trituration with diethyl ether
Mp: 135–136° C.
¹H NMR (CDCl₃): δ63.79 (bs, 2H), 5.73 (bs, 1H), 6.69 (d, 2H), 6.75–6.85 (m, 2H), 7.07–7.17 (m, 4H), 7.65–7.80 (m, 4H)

EXAMPLE 11

4-(2-Aminophenylamino)-4'-tert-butylbenzophenone (Compound 111)

General procedure 4
Starting compound II: 211
Purification: Chromatography using ethyl acetate/pentane 1:2 as eluant
Mp: 183–185° C.
¹H NMR (CDCl₃): δ1.34 (s, 9H), 3.81 (s, 2H), 5.80 (bs, 1H), 6.68 (d, 2H), 6.77 (m, 2H), 7.05–7.15 (m, 2H), 7.45 (d, 2H), 7.66 (d, 2H), 7.74 (d, 2H)

EXAMPLE 12

4-(2-Aminophenylamino)-3'-fluorobenzophenone (Compound 112)

General procedure 4
Starting compound II: 212
Purification: Trituration with diethyl ether
Mp: 115–116° C.
¹H NMR (CDCl₃): δ3.80 (bs, 2H), 5.73 (bs, 1H), 6.70 (d, 2H), 6.75–6.85 (m, 2H), 7.07–7.27 (m, 3H), 7.35–7.52 (m, 3H), 7.70 (d, 2H)

EXAMPLE 13

4-(2-Aminophenylamino)-2'-chlorobenzophenone (Compound 113)

General procedure 4
Starting compound II: 213
Mp: 182–183° C.
¹H NMR (CDCl₃): δ3.77 (bs, 2H), 5.75 (bs, 1H), 6.66 (d, 2H), 6.72–6.85 (m, 2H), 7.07–7.15 (m, 2H), 7.30–7.45 (m, 4H), 7.66 (d, 2H)

EXAMPLE 14

4-(2-Aminophenylamino)-3'-chlorobenzophenone (Compound 114)

General procedure 4
Starting compound II: 214
Purification: Trituration with diethyl ether
Mp: 107–108° C. (sublimates)
¹H NMR (CDCl₃): δ3.00 (bs, 2H), 5.73 (bs, 1H), 6.70 (d, 2H), 6.75–6.85 (m, 2H), 7.07–7.17 (m, 2H), 7.37 (t, 1H), 7.50 (m, 1H), 7.58 (m, 1H), 7.70 (m, 3H)

EXAMPLE 15

4-(2-Aminophenylamino)-2'-methoxybenzophenone (Compound 115)

General procedure 4
Starting compound II: 215
¹H NMR (CDCl₃): δ3.72 (s, 3H), 3.77 (bs, 2H), 5.57 (bs, 1H), 6.63 (d, 2H), 6.77 (m, 2H), 6.95–7.15 (m, 4H), 7.26 (m, 1H), 7.40 (m, 1H), 7.68 (d, 2H)

EXAMPLE 16

4-(2-Aminophenylamino)-3'-(dimethylamino) benzophenone (Compound 116)

General procedure 4
Starting compound II: 216
¹H NMR (CDCl₃): δ2.96 (s, 6H), 3.79 (bs, 2H), 5.69 (bs, 1H), 6.68 (d, 2H), 6.75–6.90 (m, 3H), 7.00 (bd, 1H), 7.05–7.16 (m, 3H), 7.26 (d, 1H), 7.76 (d, 2H)

EXAMPLE 17

4-(2-Aminophenylamino)-4'-chlorobenzophenone (Compound 117)

General procedure 4
Starting compound II: 217
Purification: Trituration with diethyl ether
Mp: 164–167° C.
¹H NMR (CDCl₃): δ3.80 (bs, 2H), 5.60 (bs, 1H), 6.70 (d, 2H), 6.75–6.85 (m, 2H), 7.07–7.17 (m, 2H), 7.41 (d, 2H), 7.65–7.75 (m, 4H)

EXAMPLE 18

4-(2-Aminophenylamino)-3'-methylbenzophenone (Compound 118)

General procedure 4
Starting compound II: 218

Purification: Trituration with diethyl ether
Mp: 119–120° C.
$^1$H NMR (CDCl$_3$): δ2.39 (s, 3), 3.80 (bs, 1H), 5.75 (bs, 1H), 6.70 (d, 2H), 6.75–6.85 (m, 2H), 7.05–7.17 (m, 2H), 7.31 (m, 2H), 7.47–7.55 (m, 2H), 7.72 (d, 2H)

EXAMPLE 19

3-Amino-4-(4-aminophenylamino)benzophenone (Compound 119)

General procedure 3
Starting compound II: 219
Mp: 151–153° C.
$^1$H NMR (DMSO-d$_6$): δ4.92 (s, 2H), 4.96 (bs, 2H), 6.58 (d, 2H), 6.67 (d, 1H), 6.89 (m, 3H), 7.06 (s, 1H), 7.16 (d, 1H), 7.45–7.65 (m, 5H)

EXAMPLE 20

4-(2-Aminophenylamino)-4'-n-pentylbenzophenone (Compound 120)

General procedure 4
Starting compound II: 220
Purification: Chromatography using ethyl acetate/pentane 1:2 as eluant
$^1$H NMR (CDCl$_3$): δ0.91 (t, 3H), 1.30–1.50 (m, 4H), 1.70 (m, 21H), 2.99 (t, 2), 3.80 (bs, 2H), 5.70 (bs, 1H), 6.70 (d, 2H), 6.75–6.85 (m, 2H), 7.05–7.20 (m, 2H), 7.30 (d, 2H), 7.66 (d, 2H), 7.71 (d, 2H)

EXAMPLE 21

4'-(2-Aminophenylamino)-4-chloro-2-(isopropylthio)benzonhenone (Compound 121)

General procedure 4
Starting compound II: 221
Purification: Chromatography using ethyl acetate/pentane 1:3 as eluant
$^1$H NMR (CDCl$_3$): δ1.21 (d, 6H), 3.38 (m, 1H), 3.77 (bs, 2H), 5.80 (bs, 1H), 6.65 (d, 2H), 6.72–6.85 (m, 2H), 7.05–7.15 (m, 2H), 7.20 (m, 2H), 7.45 (bs, 1H) 7.63 (d, 2H)

EXAMPLE 22

4-(2-Aminophenylamino)-4'-(trifluoromethyl)benzophenone (Compound 122)

General procedure 4
Starting compound II: 222
Purification: Chromatography using ethyl acetate/pentane 1:4 as eluant
Mp: 83–85° C.
$^1$H NMR (CDCl$_3$): δ3.80 (bs, 2H), 5.76 (bs, 1H), 6.65–6.85 (m, 4H), 7.12 (m, 2H), 7.65–7.85 (m, 6H)

EXAMPLE 23

N-(2-(4-Benzoylphenylamino)phenyl)ethanesulfonamide (Compound 123)

General procedure 5
Starting compound I: 101
Mp: 174–175° C.
$^1$H NMR (DMSO-d$_6$): δ1.12 (t, 3H), 3.01 (q, 2H), 6.96 (d, 2H), 7.15 (dt, 1H), 7.24 (dt, 1H), 7.42 (dt, 2H), 7.50–7.70 (m, 7H), 8.17 (s, 1H), 9.03 (bs, 1H)

EXAMPLE 24

N-(2-(4-Benzoylphenylamino)phenyl)benzenesulfonamide (Compound 124)

General procedure 5
Starting compound I: 101
Mp: 175–177° C.
$^1$H NMR (DMSO-d$_6$): δ6.69 (d, 2H), 7.03 (t, 1H), 7.15–7.45 (m, 6H), 7.53–7.70 (m, 9H), 7.99 (s, 1H), 9.59 (s, 1H)

EXAMPLE 25

N-(4-(4-Benzoylphenylamino)phenyl)methanesulfonamide (Compound 125)

General procedure 5
Starting compound I: 101
Mp: 179–180° C.
$^1$H NMR (DMSO-d$_6$): δ2.96 (s, 3H), 7.05 (d, 2H), 7.20 (s, 4H), 7.50–7.70 (m, 7H), 8.86 (s, 1H), 9.54 (bs, 1H)

EXAMPLE 26

N-(2-(4-Benzoylphenylamino)phenyl)methanesulfonamide (Compound 126)

General procedure 5
Starting compound I: 101
Mp: 146–148 ° C.
$^1$H NMR (DMSO-d$_6$): δ2.92 (s, 3H), 6.99 (d, 2H), 7.17 (dt, 1H), 7.25 (dt, 1H), 7.43 (m, 2H), 7.50–7.70 (m, 7H), 8.17 (s, 1H), 9.03 (bs, 1H)

EXAMPLE 27

N-(2-(4-Benzoylphenylamino)phenyl)-4-toluenesulfonamide (Compound 127)

General procedure 5
Starting compound I: 101
Mp: 194–195° C.
$^1$H NMR (DMSO-d$_6$): δ2.10 (s, 3H), 6.62 (d, 2H), 7.00–7.70 (m, 15H), 7.95 (s, 1H), 9.47 (bs, 1H)

EXAMPLE 28

1-(2-(4-Benzoylphenylamino)phenyl)-3-phenylurea (Compound 128)

To a solution of 4-(2-aminophenylamino)benzophenone (Compound 101, 0.58 g, 2 mmol) in toluene (10 ml) was added phenylisocyanate (0.22 ml, 2 mmol). The reaction mixture was heated for 20 hours on a steam bath. After cooling the reaction mixture to room temperature the resulting precipitate was collected by filtration and washed with toluene. The crude product was dissolved in hot isopropanol and crystallized on the addition of water to afford the title compound.
Mp: 154–156° C.
$^1$H NMR (DMSO-d$_6$): δ6.79 (d, 2H), 6.95 (t, 1H) 7.06 (dt, 1H), 7.20 (dt, 1H), 7.24 (m, 3H), 7.43 (d, 2H), 7.47 (m, 2H), 7.66 (m, 5H), 8.09 (dd, 1H), 8.18 (s, 1H), 8.35 (s, 1H), 9.21 (s, 1H)

EXAMPLE 29

N-(2-(4-Benzoylphenylamino)phenyl)acetamide (Compound 129)

4-(2-Aminophenylamino)benzophenone (Compound 101, 0.58 g, 2 mmol) was dissolved in acetic anhydride (10 ml) and the solution was stirred at room temperature for 3 hours. The precipitate that forms after 75 min was filtered off and washed with water to afford the title compound.

Mp: 155–157° C.

$^1$H NMR (DMSO-d$_6$): δ2.03 (s, 3H), 6.90 (d, 2H), 7.07–7.20 (m, 2H), 7.36 (dd, 1H), 7.50–7.70 (m, 8H), 8.17 (s, 1H), 9.45 (bs, 1H)

EXAMPLE 30

4-(2-Aminophenylamino)benzophenone oxime (Compound 130)

To a solution of 4-(2-aminophenylamino)benzophenone (compound 101, 0.58 g, 2 mmol) and hydroxylamine hydrochloride (0.42 g, 6 mmol) in ethanol (30 ml) was added sodium acetate (0.49 g, 6 mmol). The reaction mixture was refluxed for 30 hours, cooled to room temperature, filtered, and evaporated in vacuo. The residue was treated with water (10 ml) and diluted ammonium hydroxide (5 ml). The precipitate that forms was filtered off, washed with water and dried to afford the title compound.

Mp: 89–91° C.

$^1$H NMR (DMSO-d$_6$): δ4.75 (bs, 1H), 4.79 (bs, 1H), 6.50–7.50 (m, 14H), 10.8 (s, 0.5H), 11.10 (bs, 0.5H)

EXAMPLE 31

4-(2-Aminophenylamino)benzophenone O-methyloxime (Compound 131)

To a solution of 4-(2-aminophenylamino)benzophenone (Compound 101. 0.29 g, 1mmol) and O-methylhydroxylamine hydrochloride (0.30 g, 3.5 mmol) in ethanol (10 ml) was added sodium acetate (0.30 g, 4 mmol). The reaction mixture was refluxed for 25 hours, cooled to room temperature, filtered, and evaporated in vacuo. The residue was treated with diluted ammonium hydroxide (10 ml) and extracted with ethyl acetate (2×25 ml). The organic phase was dried (MgSO$_4$), filtered and evaporated in vacuo. The residue was dissolved in diethyl ether and acidified with hydrochloric acid in diethyl ether. The hydrochloride of the title compound instantaneously precipitate. The precipitate was triturated with ethyl acetate and washed with diethyl ether to yield the title compound as a hydrochloride.

Mp: 186–187° C. (as hydrochloride)

$^1$H NMR (DMSO-d$_6$): (as hydrochloride) δ3.88+3.82 (2s, 3H), 6.90–7.50 (m, 13H), 8.61 (bs, 3H), 9.75 (vbs, 1H)

EXAMPLE 32

Ethyl N-(2-(4-benzoylphenylamino)phenyl) carbamate (Compound 132)

General procedure 6, but replacing methyl iodide with ethyl chloroformate

Starting compound I: 101

Purification: Chromatography using ethyl acetate/pentane 1:4 as eluant

Mp: 112–114° C.

$^1$H NMR (DMSO-d$_6$): δ1.20 (t, 3H), 4.09 (q, 2H), 6.87 (d, 2H), 7.13 (m, 2H), 7.32 (m, 1H), 7.50–7.70 (m, 8H), 8.20 (s, 1H), 8.75 (s, 1H)

EXAMPLE 33

Ethyl 2-(2-(4-benzoylphenylamino)phenylamino) acetate (Compound 133)

General procedure 6, but replacing methyl iodide with ethyl bromoacetate

Starting compound I: 101

Purification: Chromatography using ethyl acetate/pentane 3:7 as eluant

Mp: 152–156° C. (as hydrochloride)

$^1$H NMR (DMSO-d$_6$): (as hydrochloride) δ1.18 (t, 3H), 3.96 (s, 2H), 4.10 (q, 2H), 6.58 (d, 1H), 6.65–6.80 (m, 3H), 7.07 (m, 2H), 7.45–7.65 (m, 7H), 7.70 (vbs, 3H)

EXAMPLE 34

4-(2-(Methylamino)phenylamino)benzophenone (Compound 134)

General procedure 6

Starting compound I: 101

Mp: 131–133 ° C.

$^1$H NMR (DMSO-d$_6$): δ2.72 (d, 3H), 5.06 (q, 1H), 6.55–6.72 (m, 4H), 7.08 (m, 2H), 7.45–7.65 (m, 7H), 8.02 (s, 1H)

EXAMPLE 35

4-(2-(Dimethylamino)phenylamino)benzophenone (Compound 135)

General procedure 6, but using 5 mmol methyl iodide

Starting compound I: 101

Mp: 99–101

$^1$H NMR (DMSO-d$_6$): δ2.63 (s, 6H), 6.95–7.12 (m, 5H), 7.27 (dd, 1H), 7.50–7.67 (m, 7H), 8.18 (s, 1H)

EXAMPLE 36

4'-(2-Aminophenylamino)-3,4,5-trimethoxybenzophenone (Compound 136)

General procedure 4

Starting compound II: 223

Purification: Chromatography using ethyl acetate/pentane 1:4 followed by 1:1 as eluant Mp: sublimate at 60° C.

$^{13}$C NMR (CDCl$_3$): δ194.3, 152.8, 150.0, 142.8, 141.2, 134.0, 132.7, 127.8, 127.4, 126.8, 125.9, 119.1, 116.4, 113.2, 107.3, 61.0, 56.3

EXAMPLE 37

N-(2-Aminophenyl)-N-methyl-4-aminobenzophenone (Compound 137)

General procedure 3

Starting compound II: 224

Purification: Crystallization from diethylether as hydrochloride

Mp: 169–172° C.

$^1$H NMR (DMSO-d$_6$): δ8.5–5.5 (bs, 3H), 7.63 (m, 4H), 7.52 (m, 2H), 7.36 (bd, 2H), 7.23 (m, 3H), 6.64 (d, 2H), 3.26 (s, 3H)

EXAMPLE 38

4-(2-Aminophenylamino)-2'-methylbenzophenone (Compound 138)

General procedure 4

Starting compound II: 225

Purification: Trituration from diethyl ether

Mp: 168–170° C.
$^{13}$C NMR (CDCl$_3$): δ197.0, 150.5, 142.8, 139.7, 135.8, 132.7, 130.6, 129.4, 128.1, 127.6, 127.4, 126.8, 125.6, 125.1, 119.1, 116.3, 113.2, 19.7

EXAMPLE 39

4'-(2-Aminophenylamino)-3'-ethylenedioxybenzophenone (Compound 139)

General procedure 4

Starting compound II: 227

Purification: Chromatography using ethyl acetate/pentane 1:2 as eluant

Mp: 168–170° C.
$^{13}$C NMR (DMSO-d$_6$): δ192.0, 150.7, 146.4, 143.6, 142.8, 131.9, 131.6, 125.9, 125.6, 124.9, 123.0, 118.1, 116.6, 116.3, 115.4, 112.4, 64.3, 63.9

EXAMPLE 40

4-(2-Aminophenylamino)-2,4'-dichlorobenzophenone (Compound 140)

General procedure 4

Starting compound II: 228

Purification: Trituration from diethyl ether $^{13}$C NMR (CDCl$_3$): δ193.7, 149.2, 142.9, 139.3, 136.3, 134.1, 132.3, 131.4, 128.7, 127.7, 127.4, 126.9, 125.4, 119.2, 116.4, 115.1, 112.0

EXAMPLE 41

4'-(2-Aminophenylamino)-2,4-dichlorobenzophenone (Compound 141)

General procedure 4

Starting compound II: 226

Purification: Trituration from diethyl ether $^{13}$C NMR (CDCl$_3$): δ192.3, 151.1, 142.8, 137.8, 135.8, 132.7, 132.1, 129.8, 129.8, 127.7, 127.0, 126.9, 126.7, 125.3, 119.1, 116.4, 113.3

EXAMPLE 42

4-(2-Aminophenylamino)-4'-(1-methylbutyloxy)benzophenone (Compound 142)

General procedure 4

Starting compound II: 229

Purification: Chromatography using ethyl acetate/pentane 1:2 as eluant $^{13}$C NMR (CDCl$_3$): δ194.2, 161.4, 149.5, 142.8, 132.5, 132.1, 130.7, 128.5, 127.2, 126.6, 126.2, 119.1, 116.3, 114.8, 113.2, 73.7, 38.5, 19.7, 18.7, 14.0

EXAMPLE 43

4-(2-Aminophenylamino)-3'-(trifluoromethyl)benzophenone (Compound 143)

General procedure 4

Starting compound II: 232

Purification: Chromatography using ethyl acetate/pentane 1:2 as eluant $^{13}$C NMR (CDCl$_3$): δ193.6, 150.5, 142.9, 139.6, 132.9, 132,6, 130.7, 128.7, 127.9, 127.6, 127.0, 126.9, 126.2, 125.6, 123.8, 119.2, 116.4, 113.3

EXAMPLE 44

4'-(2-Aminophenylamino)-2,3-dimethoxybenzophenone (Compound 144)

General procedure 4

Starting compound II: 230

Purification: Crystallization from methanol $^{13}$C NMR (CDCl$_3$): δ194.3, 152.7, 150.4, 146.5, 142.8, 135.1, 132.6. 128.1, 127.3, 126.8, 125.7, 123.9, 120.3, 119.1, 116.3, 113.6, 113.1, 61.8, 55.9

EXAMPLE 45

4-(2-Aminophenylamino)-3'-butoxybenzophenone (Compound 145)

General procedure 4

Starting compound II: 231

Purification: Chromatography using ethyl acetate/pentane 1:2 as eluant $^{13}$C NMR (CDCl$_3$): δ195.1, 159.0, 150.0, 142.8, 140.1, 132.8, 129.0, 127.9, 127.3, 126.8, 125.9, 122.0, 119.1, 118.3, 116.4, 114.8, 113.2, 67.9, 31.3, 19.2, 13.8

EXAMPLE 46

4-(2-Aminophenylamino)-4'-ethoxybenzophenone (Compound 146)

General procedure 4

Starting compound II: 235

Purification: Chromatography using ethyl acetate/pentane 1:2 as eluant $^{13}$C NMR (CDCl$_3$): δ194.2, 162.0, 149.5, 142.8, 132.5, 132.0, 131.0, 128.5, 127.2, 126.6, 126.2, 119.1, 116.3, 113.8, 113.2, 63.7, 14.7

EXAMPLE 47

4'-(2-Aminophenylamino)-3,5-dichlorobenzophenone (Compound 147)

General procedure 4

Starting compound II: 233

Purification: Crystallization from ethanol $^{13}$C NMR (DMSO-d$_6$): δ190.4, 151.7, 143.7, 142.2, 134.1, 132.4, 130.3, 127.1, 126.3, 125.9, 124.4, 124.0, 116.3, 115.5, 112.6

EXAMPLE 48

4-(2-Aminophenylamino)-4'-benzyloxybenzophenone (Compound 148)

General procedure 4

Starting compound II: 234

Purification: Crystallization from ethanol $^{13}$C NMR (CDCl$_3$): δ194.1, 161.7, 149.6, 142.8, 136.4, 132.5, 132.0, 131.4, 128.7, 128.4, 128.2, 127.5, 127.2, 126.6, 126.1, 119.1, 116.3, 114.2, 113.2, 70.1

EXAMPLE 49

4'-(2-Aminophenylamino)-3-methoxy-4-methylbenzophenone (Compound 149)

General procedure 4

Starting compound II: 237

Purification: Chromatography using ethyl acetate/pentane 1:2 as eluant $^{13}$C NMR (CDCl$_3$): δ195.0, 157.7, 149.8, 142.8, 137.5, 132.7, 131.1, 129.8, 128.2, 127.3, 126.7, 126.0, 122.6, 119.1, 116.3, 113.2, 110.6, 55.4, 16.4

EXAMPLE 50

4-(4-Amino-2-chlorophenylamino)benzophenone (Compound 150)

General procedure 3

Starting compound II: 236

Purification: Chromatography using ethyl acetate/pentane 3:7 as eluant

Mp: 133–134° C.

$^1$H NMR (DMSO-d$_6$): δ8.25 (bs, 1H), 7.69–7.55 (m, 5H), 7.51 (m, 2H), 7.04 (d, 1H), 6.74 (d, 1H), 6.63 (m, 2H), 6.57 (dd, 1H), 5.40 (bs, 2H)

EXAMPLE 51

4-(2-Aminophenylamino)-4'-methoxybenzophenone (Compound 151)

General procedure 4

Starting compound II: 239

Purification: Trituration from diethyl ether $^{13}$C NMR (CDCl$_3$): δ194.2, 162.5, 149.6, 142.8, 132.5, 132.0, 131.2, 128.4, 127.2, 126.6, 126.1, 119.1, 116.3, 113.4, 113.2, 55.4

EXAMPLE 52

4-(2-Aminophenylamino)-2-chlorobenzophenone (Compound 152)

General procedure 4

Starting compound II: 238

Purification: Trituration from diethyl ether $^{13}$C NMR (CDCl$_3$): δ194.9, 148.9, 142.9, 137.9, 134.1, 132.9, 132.3, 130.0, 128.3, 127.9, 127.5, 126.8, 125.6, 119.2, 116.4, 115.1, 111.9

EXAMPLE 53

4-(2-Aminophenylamino)-3-methylbenzophenone (Compound 153)

General procedure 4

Starting compound II: 240

$^{13}$C NMR (CDCl$_3$): δ195.4, 148.2, 142.9, 138.9, 133.1, 131.4, 131.1, 129.6, 128.0, 127.6, 127.4, 127.2, 126.0, 121.9, 119.2, 116.3, 111.2, 17.5

EXAMPLE 54

4-(2-Aminophenylamino)-3'-phenylbenzophenone (Compound 154)

General procedure 4

Starting compound II: 242

Purification: Chromatography using methylene chloride as eluant $^{13}$C NMR (CDCl$_3$): δ195.1, 150.0, 142.8, 141.1, 140.4, 139.4, 132.9, 130.1, 128.9, 128.6, 128.4, 128.2, 127.9, 127.7, 127.4, 127.2, 126.8, 125.8, 119.2, 116.4, 113.2

EXAMPLE 55

4-(2-Aminophenylamino)-2'-phenylbenzophenone (Compound 155)

General procedure 4

Starting compound II: 241

Purification: Crystallization from methylene chloride

Mp: 195–196° C.

$^{13}$C NMR (DMSO-d$_6$): δ194.9, 151.1, 143.5, 140.1, 139.5, 139.5, 131.8, 129.8, 129.4, 128.4, 128.2, 127.7, 127.0, 126.9, 126.0, 125.8, 125.6, 124.6, 116.3, 115.4, 112.3

EXAMPLE 56

4-(2-Aminophenylamino)-2-chloro-2'-methylbenzophenone (Compound 156)

General procedure 4

Starting compound II: 243

Purification: Chromatography using ethyl acetate/pentane 1:4 as eluant followed by trituration from diethyl ether Mp: 113–116° C.

$^{13}$C NMR (CDCl$_3$): δ196.5, 149.5, 142.9, 139.3, 137.7, 135.2, 133.7, 131.2, 130.7, 129.5, 128.2, 127.7, 126.9, 125.3, 119.2, 116.4, 115.3, 111.8, 20.4

EXAMPLE 57

4-(2-Aminophenylamino)-4'-phenylbenzophenone (Compound 157)

General procedure 4

Starting compound II: 245

Purification: Trituration from methylene chloride

Mp: 179–182° C.

$^{13}$C NMR (DMSO-d$_6$): δ193.0, 151.0, 143.6, 142.8, 139.1, 137.4, 132.1, 129.7, 129.0, 128.0, 126.8, 126.4, 126.0, 125.7, 125.3, 124.8, 116.3, 115.4, 112.5

EXAMPLE 58

4-(2-Amino-5-hydroxyphenylamino)benzophenone (Compound 158)

General procedure 3

Starting compound II: 266

Purification: Crystallized from ether as hydrochloride

Mp: >240° C. (as hydrochloride)

$^1$H NMR (DMSO-d$_6$): (as hydrochloride) δ9.98 (bs, 2H), 9.87 (bs, 2H), 9.01 (s, 1H), 7.75–7.59 (m, 5H), 7.54 (m, 2H), 7.28 (d, 1H), 7.05 (m, 2H), 6.91 (d, 1H), 6.61 (dd, 1H)

EXAMPLE 59

4-(2-Aminophenylamino)-2'-hydroxybenzophenone (Compound 159)

General procedure 4

Starting compound II: 247

Purification: Crystallization from diethyl ether $^{13}$C NMR (CDCl$_3$): δ199.3, 162.7, 149.8, 142.9, 135.4, 133.1, 132.3. 128.0, 127.4, 126.8, 125.8, 119.7, 119.2, 118.4, 118.2, 116.4, 113.3

EXAMPLE 60

4-(4-Aminophenylamino)-2'-methylbenzophenone (Compound 160)

General procedure 4

Starting compound II: 246

Purification: Chromatography using ethyl acetate/pentane 1:1 as eluant followed by trituration from diethyl ether Mp: 143–144° C.

$^{13}$C NMR (CDCl$_3$): δ196.9, 151.1, 143.9, 139.9, 135.8, 132.7, 130.9, 130.6, 129.3, 127.6, 125.4, 125.1, 115.9, 112.8, 19.7

EXAMPLE 61

4-(2-Aminophenylamino)-3'-cyanobenzophenone (Compound 161)

General procedure 4

Starting compound II: 244

Purification: Chromatography using ethyl acetate/pentane 1:1 as eluant followed by trituration from methylene chloride Mp: 146–149° C.

$^{13}$C NMR (CDCl$_3$): δ192.6, 150.8, 142.9, 140.0, 134.5, 133.4, 133.0, 132.9, 129.2, 127.7, 127.0, 126.5, 125.4, 119.2, 118.2, 116.4, 113.4, 112.5

EXAMPLE 62

4-(2-Aminophenylamino)-2'-phenoxymethylbenzophenone (Compound 162)

General procedure 4

Starting compound II: 249

Purification: Trituration from diethyl ether

Mp: 156–159° C.

$^{13}$C NMR (CDCl$_3$): δ195.9, 158.5, 150.5, 142.8, 138.4, 136.3, 132.9, 130.0, 129.3, 128.4, 128.2, 128.1, 127.5, 127.0, 126.8, 125.7, 120.9, 119.2, 116.4, 114.9, 113.2, 67.4

EXAMPLE 63

4-(2-Aminophenylamino)-2'-bromobenzophenone (Compound 163)

General procedure 4

Starting compound II: 250

Mp: 156–161° C.

$^{13}$C NMR (CDCl$_3$): δ194.0, 150.9, 142.8, 141.5, 133.0, 132.9, 130.5, 128.6, 127.5, 127.0, 127.0, 126.7, 125.4, 119.4, 119.1, 116.4, 113.3

EXAMPLE 64

4'-(2-Aminophenylamino)-2,3,5,6-tetramethylbenzophenone (Compound 164)

General procedure 4

Starting compound II: 251

$^{13}$C NMR (CDCl$_3$): δ199.7, 150.6, 142.8, 140.5, 134.0, 132.0, 131.4, 129.6, 128.6, 127.4, 126.9, 125.7, 119.1, 116.3, 113.4, 19.5, 16.3

EXAMPLE 65

4-(2-Aminophenylamino)-2'-ethylbenzophenone (Compound 165)

General procedure 4

Starting compound II: 248

Purification: Chromatography using ethyl acetate/pentane 1:2 as eluant $^{13}$C NMR (CDCl$_3$): δ197.1, 150.5, 142.8, 142.2, 139.4, 132.7, 129.5, 129.1, 128.4, 127.6, 127.4, 126.9, 125.7, 125.1, 119.1, 116.4, 113.2, 26.3, 15.8

EXAMPLE 66

4-(3-Aminophenylamino)benzophenone (Compound 166)

General procedure 4

Starting compound II: 4-(3-nitrophenylamino)benzophenone

Purification: Chromatography using ethyl acetate/pentane 1:2 as eluant $^{13}$C NMR (CDCl$_3$): δ195.2, 148.2, 147.7, 141.7, 138.7, 132.7, 131.5, 130.3, 129.6, 128.5, 128.1, 114.6, 110.8, 110.3, 106.9

EXAMPLE 67

4-(4-Aminophenylamino)-2'-hydroxybenzophenone (Compound 167)

General procedure 4

Starting compound II: 4'-(4-nitrophenylamino)-2'-hydroxybenzophenone

Purification: Chromatography using ethyl acetate/pentane 1:4 as eluant $^{13}$C NMR (CDCl$_3$): δ199.1, 162.6, 150.5, 143.8, 135.2, 133.1, 132.4. 131.1, 127.3, 125.3, 119.8, 118.3, 118.1, 116.0, 112.8

EXAMPLE 68

4-(2-Aminophenylamino)-2',3-dimethylbenzophenone (Compound 168)

General procedure 4

Starting compound II: 253

Purification: Chromatography using ethyl acetate/pentane 1:4 as eluant $^{13}$CNMR (CDCl$_3$): δ197.3, 148.7, 142.9, 139.8, 135.9, 132.7, 131.1, 130.6, 129.3, 128.0, 127.7, 127.5, 127.3, 125.8, 125.1, 121.9, 119.2, 116.4, 111.3, 19.7, 17.5

EXAMPLE 69

4-(2-Aminophenylamino)-3-methoxy-2'-methylbenzophenone (Compound 169)

General procedure 4

Starting compound II: 252

Purification: Chromatography using ethyl acetate/pentane 1:2 as eluant $^{13}$C NMR (CDCl$_3$): δ197.1, 146.6, 142.9, 140.8, 139.8, 135.8, 130.6, 129.3, 127.6, 127.5, 127.4, 127.2, 126.9, 125.4, 125.0, 119.0, 116.2, 109.9, 109.6, 55.8, 19.7

EXAMPLE 70

4-(2-Aminophenylamino)-2-methoxy-2'-methylbenzophenone (Compound 170)

To a solution of 2-methoxy-2'-methyl-4-(2-nitrophenylamino)benzophenone (Compound 255, 1.02 g, 2.8 mmol) in methanol (10 ml) was added, under argon, ammonium formiate (0.80 g, 13 mmol) and 10% palladium on carbon (0.16 g). The reaction mixture was stirred at room temperature for 16 hours. The mixture was filtered through Celite® and evaporated in vacuo. The residue was treated with water (50 ml) and extracted with methylene chloride (2×50 ml). The organic phase was dried (MgSO$_4$), filtered and evaporated in vacuo to afford the crude product which was further purified by chromatography using ethyl acetate/pentane 1:1 as eluant.

Mp: 122–125° C.

$^{13}$C NMR (CDCl$_3$): δ196.5, 161.8, 151.4, 142.8, 141.8, 135.9, 134.9, 130.5, 129.2, 127.9, 127.3, 126.7, 125.8, 125.0, 119.1, 119.0, 116.4, 105.9, 97.0, 55.5, 19.9

EXAMPLE 71

4-(2-Aminophenylamino)-2'-tert-butoxybenzophenone (Compound 171)

By following the procedure of example 70, but using 2-tert-butoxy-4'-(2-nitrophenylamino)benzophenone (Compound 256) in place of 2-methoxy-2'-methyl-4-(2-nitrophenylamino)benzophenone (Compound 255), the desired compound was obtained.

Purification: Chromatography using ethyl acetate/pentane 1:2 as eluant $^{13}$C NMR (CDCl$_3$): δ195.7, 153.3, 149.9, 142.6, 135.7, 132.5, 130.4, 129.4, 128.9, 127.1, 126.5, 126.1, 123.0, 122.8, 119.1, 116.4, 113.1, 80.1, 28.9

EXAMPLE 72

4-(2-Aminophenylamino)-2-chloro-2'-(trifluoromethyl)benzophenone (Compound 172)

General procedure 4

Starting compound II: 257

Purification: Chromatography using ethyl acetate/pentane 1:2 as eluant

Mp: 128–129° C.

$^{13}$C NMR (CDCl$_3$): δ192.8, 150.6, 143.0, 140.2, 136.7, 135.3, 131.4, 129.8, 128.4, 128.0, 128.0, 127.2, 126.8, 125.6, 124.7, 123.7, 119.2, 116.5, 115.5, 111.6

EXAMPLE 73

Ethyl N-(2-(4-(2-methylbenzoyl)-3-chlorophenylamino)phenyl)carbamate (Compound 173)

General procedure 6, but replacing methyl iodide with ethyl chloroformate

Starting compound I:156

Purification: Chromatography using ethyl acetate/pentane 1:4 as eluant $^{13}$C NMR (CDCl$_3$): δ196.6, 154.1, 149.1, 139.1, 138.0, 135.0, 133.5, 133.4, 131.3, 130.9, 130.5, 129.7, 129.2, 126.9, 126.0, 125.4, 124.9, 121.7, 116.1 112.5, 61.7, 20.5, 14.5

EXAMPLE 74

4'-(2-Aminophenylamino)-3'-chloro-4-methoxy-2,6-dimethylbenzophenone (Compound 174)

General procedure 4

Starting compound II: 259

Purification: Crystallization from diethyl ether

Mp: 158–159° C.

$^{13}$C NMR (CDCl$_3$): δ197.1, 159.6, 150.1, 142.9, 136.6, 136.0, 134.6, 134.0, 127.8, 127.2, 127.0, 125.0, 119.2, 116.4, 115.9, 113.1, 111.8, 55.1, 20.0

EXAMPLE 75

4-(4-Aminophenylamino)-2-chloro-2'-methylbenzophenone (Compound 175)

General procedure 4

Starting compound II: 261

Purification: Chromatography using ethyl acetate/pentane 1:4 as eluant $^{13}$C NMR (DMSO-d$_6$): δ194.8, 151.2, 145.9, 139.8, 135.9, 134.0, 134.0, 130.8, 130.2, 128.3, 128.1, 125.5, 124.6, 124.4, 114.5, 113.5, 110.5, 19.5

EXAMPLE 76

4-(2-Aminophenylamino)-2'-allyloxybenzophenone (Compound 176)

General procedure 4

Starting compound II: 254

Purification: Chromatography using ethyl acetate/pentane 1:4 followed by 1:2 as eluant $^{13}$C NMR (CDCl$_3$): δ194.6, 155.9, 150.1, 142.7, 132.9, 132.5, 130.9, 130.2, 129.2, 128.7. 127.2, 126.6, 126.0, 120.7, 119.1, 116.9, 116.3, 113.1, 112.9, 69.1

EXAMPLE 77

4-(2-Amino4-methylphenylamino)-2-chloro-2'-methylbenzophenone (Compound 177)

General procedure 4

Starting compound II: 260

$^{13}$C NMR (CDCl$_3$): δ195.7, 150.0, 142.9, 139.5, 137.9, 137.7, 135.3, 133.8, 131.2, 130.6, 129.5, 128.0, 127.3, 125.3, 122.5, 120.0, 116.9, 115.1, 111.5, 21.2, 20.4

EXAMPLE 78

4-(2-Aminophenylamino)-2-chloro-2'-methoxybenzophenone (Compound 178)

General procedure 4

Starting compound II: 262

Purification: Chromatography using ethyl acetate/pentane 1:2 as eluant

Mp: 67–69° C.

$^{13}$C NMR (CDCl$_3$): δ193.7, 158.1, 149.2, 142.8, 135.0, 133.6, 132.5, 130.4, 129.9, 128.7, 127.5, 126.7, 125.5, 120.5, 119.1, 116.4, 115.2, 111.8, 111.6, 55.9

EXAMPLE 79

3-Allyl-4'-(2-aminophenylamino)-2-hydroxybenzophenone (Compound 179)

General procedure 4

Starting compound II: 258

Purification: Chromatography using ethyl acetate/pentane 1:9 as eluant $^{13}$C NMR (DMSO-d$_6$): δ197.5, 158.1, 151.2, 143.8, 136.4, 134.6, 132.2, 130.2, 128.3, 126.2, 125.9, 125.5, 124.8, 120.7, 118.5, 116.5, 116.0, 115.5, 112.5, 33.2

EXAMPLE 80

4'-(2-Aminophenylamino)-2'-chloro-2,4,5-trifluorobenzophenone (Compound 180)

General procedure 4

Starting compound II: 263

Purification: Chromatography using ethyl acetate/pentane 1:3 as eluant $^{13}$C NMR (CDCl$_3$): δ184.3, 154.9, 151.1, 147.5, 147.0, 143.0, 136.5, 134.8, 128.1, 127.3, 125.7, 124.4, 120.7, 119.2, 118.4, 116.5, 115.5, 112.0, 111.4

EXAMPLE 81

2,2,2-Trifluoro-N-(2-(4-(2-methylbenzoyl)-3-chlorophenylamino)phenyl)acetamide (Compound 181)

To a cold (ice/water) solution of 4-(2-aminophenylamino)-2-chloro-2'-methylbenzophenone (Compound 156, 1.0 g, 3.0 mmol) and pyridine (0.4 ml, 4.5 mmol) in methylene chloride (10 ml) was added trifluoroaceticacidanhydride (0.46 ml, 1.1 mmol). After stirring for 30 minutes, the reaction mixture was poured into water and, extracted with ethyl acetate (2×50 ml). The organic phase was dried (MgSO$_4$), filtered and evaporated to afford the the almost pure product.

Purification: Chromatography using ethyl acetate/pentane 1:2 as eluant $^{13}$C NMR (CDCl$_3$): δ196.8, 155.2, 148.5, 138.6, 138.2, 134.9, 133.3, 131.8, 131.4, 131.2, 130.9, 130.2, 129.9, 127.6, 127.3, 126.4, 125.4, 122.9, 116.5, 15.6, 112.9, 20.5

EXAMPLE 82

4-(2-Aminophenylamino)-2-chloro-2',6'-dimethylbenzophenone (Compound 182)

General procedure 4

Starting compound II: 264

Purification: Chromatography using ethyl acetate/pentane 1:4 as eluant

Mp: 139–140° C.

$^{13}$C NMR (CDCl$_3$): δ197.2, 150.4, 142.9, 141.1, 136.3, 135.0, 134.2, 128.6, 127.9, 127.6, 127.1, 126.0, 124.8, 119.1, 116.4, 116.1, 111.7, 19.5

EXAMPLE 83

4-(2-Aminophenylamino)-2-chloro4'-fluoro-2'-methylbenzophenone (Compound 183)

General procedure 4

Starting compound II: 265

Purification: Chromatography using ethyl acetate/pentane 1:3 as eluant

Mp: 152–154° C.

$^{13}$C NMR (CDCl$_3$): δ195.3, 163.9, 149.5, 142.9, 141.5, 135.4, 135.0, 133.4, 132.3, 128.4, 127.7, 126.9, 125.3, 119.2, 118.1, 116.4, 115.3, 112.3, 111.9, 20.7

EXAMPLE 84

3-(2-(4-(2-Methylbenzoyl)-3-chlorophenylamino)phenyl)-1,1-dimethylurea (Compound 184)

A mixture of 4-(2-aminophenylamino)-2-chloro-2'-methylbenzophenone (Compound 156, 1.2 g, 3.5 mmol), dimethylcarbamyl chloride (0.32 ml, 3.5 mmol) and potassium carbonate (1.0 g, 7 mmol) in N,N-dimethylformamide (20 ml) was stirred at room temperature for 16 hours. The reaction mixture was poured into water (100 ml) and was extracted with ethyl acetate (3×75 ml). The organic phase was dried (MgSO$_4$), filtered and evaporated in vacuo to give the crude product. The crude product was purified by flash chromatography by using ethyl acetate/pentane mixtures from 1:9 to 1:1. Trituration with diethyl ether/pentane 1:1 afforded the pure title compound.

$^{13}$C NMR (CDCl$_3$): δ196.3, 150.9, 149.9, 139.8, 138.8, 136.6, 136.4, 133.1, 132.3, 132.0, 131.6, 131.0, 129.1, 127.6, 127.3, 125.7, 123.8, 123.4, 112.7, 109.0, 38.8, 37.1, 21.3

EXAMPLE 85

4-(2-(n-Butylamino)phenylamino)benzophenone (Compound 185)

General procedure 6, but using n-butylbromide in isopropanol under reflux

Starting compound I: 101

Purification: Chromatography using ethyl acetate/pentane 3:7 as eluant

Mp: 88–93° C.

$^1$H NMR (DMSO-d$_6$): δ8.03 (bs, 1H), 7.69–7.55 (m, 5H), 7.51 (m, 2H), 7.07 (m, 2H), 6.76–6.66 (m, 3H), 6.60 (m, 1H), 4.75 (t, 1H), 3.07 (q, 2H), 1.51 (m, 2H), 1.33 (m, 2H), 0.88 (t, 3H)

EXAMPLE 86

N-(4-Benzoylphenyl)-N,N'-1,2-phenylene-di(2,2,2-trifluoroacetamide) (Compound 186)

To a solution of 4-(2-aminophenylamino)benzophenone (Compound 101, 0.29 g, 1.0 mmol) and pyridine (0.25 ml, 3.0 mmol) in methylene chloride (10 ml) was added trifluoroaceticacidanhydride (0.30 ml, 2.2 mmol). After stirring for 45 minutes at room temperature, the reaction mixture was evaporated in vacuo. The residue crystallized oil trituration with water (10 ml) to afford the title compound after filtration.

$^1$H NMR (DMSO-d$_6$): δ11.5–11.1 (bs, 1H), 7.95–7.37 (m, 13H)

EXAMPLE 87

2,2,2-Trifluoro-N-(2-(4-benzoylphenylamino)phenyl)acetamide (Compound 187)

By following the procedure of example 81, but using 4-(2-aminophenylamino)-benzophenone (Compound 101) in place of 4-(2-aminophenylamino)-2-chloro-2'-methylbenzophenone (Compound 156), the desired compound was obtained.

Purification: Trituration from diethyl ether

Mp: 187–191° C.

$^1$H NMR (DMSO-d$_6$): δ10.80 (bs, 1H), 8.47 (s, 1H), 7.71–7.58 (m, 5H), 0.53 (m, 2H), 7.43 (m, 2H), 7.33 (m, 1H), 7.17 (m, 1H), 6.93 (m, 2H)

EXAMPLE 88

1-(2-(4-Benzoylphenylamino)phenyl)-3-n-propylurea (Compound 188)

To a solution of 4-(2-aminophenylamino)benzophenone (Compound 101, 0.58 g, 2 mmol) in toluene (10 ml) was added n-propylisocyanate (0.23 ml, 2.4 mmol). The reaction mixture was heated for 4 hours on a steam bath. After cooling the reaction mixture to room temperature the resulting precipitate was collected by filtration and washed with toluene. The crude product was dissolved in hot isopropanol and crystallized on cooling to afford the title compound.

Mp: 167–169° C.

$^1$H NMR (DMSO-$d_6$): δ8.25 (s, 1H), 8.03 (m, 1H), 7.86 (s, 1H), 7.70–7.56 (m, 5H), 7.51 (m, 2H), 7.81 (m, 1H), 7.12 (m, 1H), 6.97 (m, 1H), 6.75 (m, 3H), 3.02 (q, 2H), 1.41 (m, 2H), 0.85 (t, 3H)

EXAMPLE 89

N-(2-(4-Benzoylphenylamino)phenyl)formamide (Compound 189)

A solution of 4-(2-aminophenylamino)benzophenone (Compound 101 0.29 g, 1.0 mmol) in ethyl formate (5.0 ml, 63 mmol) was refluxed for 16 hours. The reaction mixture was evaporated in vacuo and dissolved i ethyl acetate. The solution was filtered and evaporated in vacuo. The residue was crystallized on the addition of diethyl ether to afford the pure title compound.

Mp: 122–124° C.

$^{13}$C NMR (DMSO-$d_6$): δ194.6, 144.0, 143.1, 139.3, 136.8, 135.6, 132.8, 132.5, 131.5, 129.6, 128.6, 123.7, 123.0, 122.8, 120.1, 110.9

EXAMPLE 90

Creme Formulation 4-(2-Aminophenylamino)benzophenone (Compound 101, 10 g) was dissolved in diethylenglycolmonoethylether (350 g) and distilled water (350 g) was added. Methylparaben (1 g) and propylparaben (0.2 g) were dissolved in phenoxyethanol (6 g). This solution was mixed with the former solution of Compound 101. Paraffin oil (183 g), cetostearylic alcohol (50 g) and ARLACEL® (50 g) was melted in a vessel at 70 to 80° C. The mixed solutions were likewise heated to 60–70° C. and slowly added to the melted oil phase under high speed stirring. The homogenized components were cooled to room temperature.

What we claim is:

1. A compound of the formula I

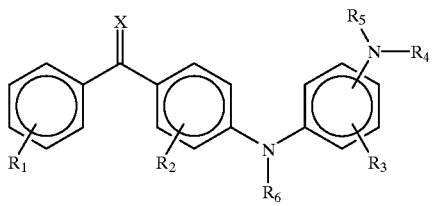

in which formula $R_1$ and $R_2$ stands independently for one or more, the same or different substituents selected from the group consisting of hydrogen, halogen, hydroxy, mercapto, trifluoromethyl, amino, alkyl, alkoxy, alkylthio, alkylamino, or alkoxycarbonyl, the C-content of which can be from 1 to 5, cyano, carbamoyl, phenyl, or nitro; $R_3$ stands for hydrogen, halogen, hydroxy, mercapto, trifluoromethyl, amino, alkyl, alkoxy, alkylthio, alkylamino, or alkylcarbonyl, the C-content of which can be from 1 to 5, phenyl, cyano, carboxy, or carbamoyl; $R_4$, $R_5$ and $R_6$ stand independently for hydrogen, trifluoromethyl, alkyl, carbamoyl, alkoxycarbonyl, or alkaloyl, the C-content of which can be from 1 to 5; X stands for oxygen, N—OH, N—O-alkyl, dialkoxy, cyclic dialkoxy, dialkylthio, or cyclic dialkythio, the C-content of which can be from 1 to 5; and salts with pharmaceutically acceptable, non-toxic acids.

2. A compound according to formula I of claim 1, in which formula $R_1$, $R_2$, $R_3$, $R_4$, $R_5$ and $R_6$ have the meanings as defined in claim 1; X stands for oxygen, N—OH, or N—O-alkyl, the C-content of which can be from 1 to 5; and salts with pharmaceutically acceptable, non-toxic acids.

3. A salt according to claim 1 in which the salt is selected from the group consisting of salts formed with hydrochloric, hydrobromic and hydroiodic acid, phosphoric acid, sulphuric acid, nitric acid, p-toluenesulphonic acid, methanesulphonic acid, formic acid, acetic acid, propionic acid, citric acid, tartaric acid, and maleic acid.

4. A compound of claim 1 which is selected from the group consisting of:

4-(2-aminophenylamino)-2-chloro-2'-methylbenzophenone;
4-(2-aminophenylamino)-2-methoxy-2'-methylbenzophenone;
4-(2-aminophenylamino)-2-chloro-2'-(trifluoromethyl)benzophenone;
ethylN-(2-(4-(2-methylbenzoyl)-3-chlorophenylamino)phenyl)carbamate;
4'-(2-aminophenylamino)-3'-chloro-4-methoxy-2,6-dimethylylbenzophenone;
2,2,2-trifluoro-N-(2-(4-(2-methylbenzoyl)-3-chlorophenylamino)phenyl)acetamide;
4-(2-aminophenylamino)-2-chloro-2',6'-dimethylbenzophenone; and
4-(2-aminophenylamino)-2-chloro-4'-fluoro-2'-methylbenzophenone;

and their salts.

5. A method for producing a compound of formula I according to claim 1, in which (a) a compound of formula III is coupled with a compound of formula IVa or IVb in a solvent in the presence of base to give a product of the formula II

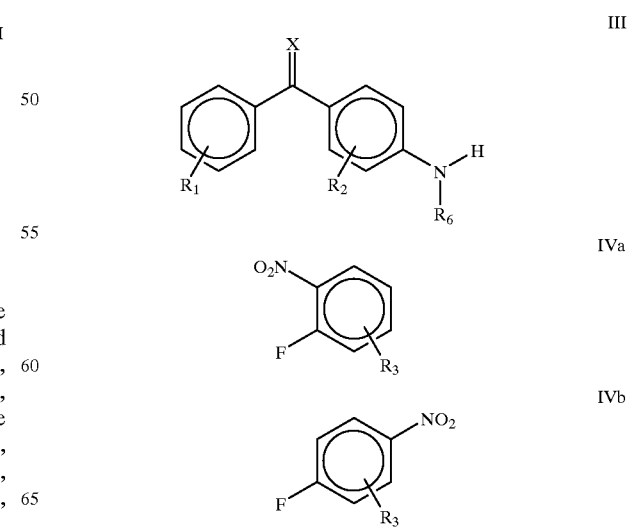

-continued

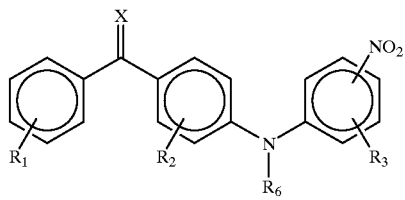

II in which X, $R_1$, $R_2$, $R_3$, and $R_6$ are as defined in claim 1;

(b) a compound of formula II is reduced with an appropriate reducing agent to form the desired compound of formula I.

6. A pharmaceutical composition comprising a compound according to claim 1 and a pharmaceutically acceptable carrier therefor.

7. A method for the treatment and prophylaxis of asthma, allergy, rheumatoid arthritis, spondyloarthritis, gout, atherosclerosis, chronic inflammatory bowel disease, proliferative and inflammatory skin disorders, which comprises administering to said patients an effective amount of one or more compounds according to claim 1.

* * * * *